US007071163B2

(12) United States Patent
Sokoloff et al.

(10) Patent No.: US 7,071,163 B2
(45) Date of Patent: Jul. 4, 2006

(54) COMPOUNDS FOR TARGETING HEPATOCYTES IN VIVO

(75) Inventors: Alexander V. Sokoloff, Madison, WI (US); So Wong, Oregon, WI (US); Jon A. Wolff, Madison, WI (US); Sean D. Monahan, Madison, WI (US); James Ludtke, Deerfield, WI (US); Lori Higgs, Madison, WI (US); Darren Wakefield, Fitchburg, WI (US); Magdolna G. Sebestyén, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 125 days.

(21) Appl. No.: 10/633,808

(22) Filed: Aug. 4, 2003

(65) Prior Publication Data

US 2004/0029826 A1    Feb. 12, 2004

Related U.S. Application Data

(60) Provisional application No. 60/401,167, filed on Aug. 5, 2002.

(51) Int. Cl.
*A61K 38/00* (2006.01)
(52) U.S. Cl. .......................... 514/12; 514/44; 530/350; 424/85.1
(58) Field of Classification Search .................. 514/12, 514/44; 530/300, 350
See application file for complete search history.

(56) References Cited

U.S. PATENT DOCUMENTS 6,471,957 B1 * 10/2002 Sim et al. ................... 424/85.2

OTHER PUBLICATIONS

Carlsson, J. et al. Biochem. J. 173: 723-737 (1978).*
Rensen, P. et al. JBC 276(40): 37577-37584 (2001).*
Studier, F.W. et al. Methods in Enzymology 185: 60-89 (1990).*
Lutz-Freyermuth, C. et al. PNAS 87: 6393-6397 (1990).*
Biessen EAL, et al. "Ligand size is a major determinant of high-affinity binding of fucose- and galactose-exposing (lipo)proteins by the hepatic fucose recepotor." *Biochem J* 1994 vol. 299 pp. 291-296.
Bijsterbosch MK, et al Native and modified lipoproteins as drug delivery systems. *Advanced Drug Delivery Reviews* 1990 vol. 5 pp. 213-251.
Chiou HC, et al. Gene therapy strategies for the treatment of chronic viral hepatitis. *Expert Opinion on Biological Therapy* 2001 vol. 1 pp. 629-639.
Fiume L, et al. Inhibition of hepatitis viral replication by vidarabine monophosphate conjugated with lactosaminated serum albumin. *Lancet* 1988 vol. 2 pp. 13-15.

Fiume L, et al. The pathogenesis of vacuoles produced in rat and mouse liver cells by a conjugate of adenine arabinoside monophosphate with lactosaminated albumin. *J Hepatology* 1992 vol. 15 pp. 314-322.
Furomoto K, et al. Biliary excretion of polystyrene micropheres depends on the type of receptor-mediated uptake in rat liver. *Biochimica et Biophysica Acta* 2001 vol. 1526 pp. 221-226.
Goldberg J, et al. Erythropoietin mimetics derived from solution phase combinatorial libraries. *J Amer Chem Soc* 2002 vol. 124 pp. 544-555.
Groman EV, et al. Arabinogalactan for hepatic drug delivery. *Bioconj Chem* 1994 vol. 5 pp. 547-556.
High KA. Gene transfer as an approach to treating hemophilia. *Circulation Research* 2001 vol. 88 pp. 137-144.
Koide A, et al. The fibronectin type III domain as a scaffold for novel binding proteins. *Journal of Molecular Biology* 1998 vol. 284 pp. 1141-1151.
Lee YC, et al. Binding of synthetic oligosaccharides to the hepatic gal/GalNAc lectin. *J Biol Chem* 1983 vol. 258 pp. 199-202.
Meiher DKF, et al. Drug targeting systems for antiviral agents: options and limitations. *Antiviral Research* 1992 vol. 18 pp. 215-258.
Nord K, et al. Binding proteins selected form combinatorial libraries of an alpha-helical bacterial receptor domain. *Nature Biotechnology* 1997 vol. 15 pp. 772-777.
Nord K, et al. A combinatorial libary of an alpha-helical bacterial receptor domain. *Protein Engineering* 1995 vol. 8 pp. 601-608.
Okuno K, et al. Hepatic immunopotentiation by galactose-entrapped liposomal IL-2 compound in the treatment of liver metastases. *Surg Today* 1998 vol. 28 pp. 64-69..
Rensen PC, et al. Determination of the upper size limit for uptake and processing of ligands by the asialoglycoprotein receptor on hepatocytes *in vitro* and *in vivo*. *Journal of Biological Chemistry* 2001 vol. 276 pp. 37577-37584.
Rogers JC, et al. Hepatic uptake of proteins coupled to fetuin glycoprotein. *Biochem Biophys Res Comm* 1971 vol. 45 pp. 622-629.
Schlepper-Schafer J, et al. Endocytosis via galactose receptors *in vivo*. Ligand size directs uptake by hepatocytes and/or liver marcophages. *Experimental Cell Research* 1986 vol. 165 pp. 494-506.
Severin E, et al. Flow cytometric analysis of mouse hepatocyte ploidy. II. The development of polyploidy pattern in four mice strains with differenct life spans. *Cell & Tissue Research* 1984 vol. 238 pp. 649-652.

(Continued)

*Primary Examiner*—Jon Weber
*Assistant Examiner*—Anand Desai
(74) *Attorney, Agent, or Firm*—Mark K. Johnson; Kirk Ekena

(57) ABSTRACT

We describe compounds that bind to and are internalized by hepatocytes. Association of these compounds to other molecules or complexes can be used to target the molecules or complexes to hepatocytes in vivo or in vitro.

20 Claims, 10 Drawing Sheets

OTHER PUBLICATIONS

Shimada K, et al. Biodistribution of liposomes containing synthetic galactose-terminated diacylglycerol-poly(ethylene)glycols. *Biochim Biophys Acta* 1997 vol. 1326 pp. 329-341.

Sokoloff AV, et al. Specific recognition of protein carboxy-terminal sequences by natural IgM antibodies in normal serum. *Molecular Therapy* 2001 vol. 3 pp. 821-830.

Sokoloff AV, et al. The interactions of peptides with the innate immune system studied with use of T7 phage peptide display. *Molecular Therapy* 2000 vol. 2 pp. 131-139.

Sokoloff AV, et al. "A new peptide ligand that targets particles and heterologous proteins to hepatocytes in vivo." *Molecular Therapy* 2003 vol. 8 No. 6 pp. 867-872.

Steven AC, et al. Molecular substructure of a viral receptor-recognition protein. The gp17 tail-fiber of bacteriophage T7. *Journal of Molecular Biology* 1988 vol. 200 pp. 351-365.

Studier FW The genetics and physiology of bacteriophage T7. *Virology* 1969 vol. 39 pp. 562-574.

Tomlinson E Theory and practice of site-specific drug delivery. *Advance Drug Delivery Reviews* 1987 vol. 1 pp. 87-98.

van Berkel JC, et al. The effect of a water-soluble tris-galactoside-terminated cholesterol derivative on the fate of low density lipoproteins and liposomes. *J Biol Chem* 1985 vol. 260 pp. 2694-2699.

Vyas SP, et al. Endogenous carriers and ligands in non-immunogenic site-specific drug delivery. *Advanced Drug Delivery Reviews* 2000 vol. 43 pp. 101-164.

Weglarz TC, et al. Hepatocyte transplantation into diseased mouse liver. Kinetics of parenchymal repopulation and identification of the proliferative capacity of tetraploid and octaploid hepatocytes. *American Journal of Patholvogy* 2000 vol. 157 pp. 1963-1974.

Wu J, et al. Targeting hepatocytes for drug and gene delivery pp. emerging novel approaches and applications. *Frontiers in Bioscience* 2002 vol. 7 pp. 717-725.

* cited by examiner

| CARGO |—| ATTACHMENT CHEMISTRY |—| LINKER |—| ATTACHMENT CHEMISTRY |—| T7 LIGAND |

A.

B.

C.

COMPOUNDS FOR TARGETING HEPATOCYTES IN VIVO

CROSS-REFERENCE TO RELATED APPLICATIONS

This application claims priority benefit of U.S. Provisional Application Ser. No. 60/401,167 filed Aug. 5, 2002.

BACKGROUND OF THE INVENTION

Hepatocytes perform important roles in the metabolism, homeostasis of serum proteins and in the pathogenesis of various metabolic and infectious disorders. They are thus an important target for pharmacological agents. Conventional therapeutic agents that act on hepatocytes include small molecules and proteins, such as nucleoside analogues (e.g., ribavirin) and interferon used for treatment of hepatitis C [Hayden 2001]. Greater efficacy and decreased toxicity would be gained by delivering such biologically active compounds to hepatocytes in a more selective manner [Tomlinson 1987; Bijsterbosch & van Berkel 1990; Meiher et al. 1992]. Hepatocytes are also a target for a variety of anti-sense and gene therapies designed to treat liver based disorders, including: hepatitis, hypercholesterolemia and hemophilia [Chiou et al. 2001; High 2001]. However, the inability to efficiently and safely deliver nucleic acids to hepatocytes has held back the promise of nucleic acid based therapies.

One important component of any hepatocyte delivery system is a ligand that serves as a targeting "address" providing for specific and efficient delivery of therapeutic vehicles to hepatocytes [Vyas & Sihorkar 2000]. Most approaches for targeting hepatocytes have relied upon ligands that react with the asialoglycoprotein receptor (AS-GPr) [Groman et al. 1994; Lee et al. 1983]. Such ligands have allowed hepatocyte targeting with small molecules, such as adenosine arabinoside, or proteins such as immunoglobulin [Rogers & Kornfeld 1971; Fiume et al. 1988]. However, there are conflicting reports concerning the utility of ASGPr ligands for targeting particles [Rensen et al. 2001; Schlepper-Schafer et al. 1986; Shimada et al. 1997; Biessen et al 1994]. A wide variety of the size limits for ASGPr-reactive particles, ranging from 10 to 70 nm, have been reported. In addition to particles and liposomes, many studies have also used ASGPr ligands for incorporation into complexes of plasmid DNA and polycations (polyplexes) [Wu et al. 2002]. The accumulated data indicate that the efficiency of hepatocyte transfection achieved with these formulations is not sufficient for clinical use.

New ligands that provide better hepatocyte specificity and potentially utilize different cellular internalization pathways would allow more flexibility in designing delivery strategies. Phage display libraries have frequently been used to identify peptide ligands that interact with specific receptors. We have previously proposed the use of T7 phage display libraries for in vivo studies because their ~60 nm size and icosahedral shape resembles the size and shape of liposomes and DNA polyplexes.

SUMMARY OF THE INVENTION

In the present invention, we describe a compound, hereafter referred to as the T7 ligand, that selectively targets hepatocytes in vivo and in vitro. We have observed that a particular bacteriophage T7 clone, when injected into the tail vein of mice, localizes to and is internalized by hepatocytes. The p17 protein of this T7 phage, contains the hepatocyte targeting determinant. More specifically, we show that a short peptide fragment of the p17 protein rod domain is sufficient to target hepatocytes. We have observed T7 phage localization to hepatocytes in mice and monkeys, indicating the T7 ligand targets hepatocytes in many and possibly all mammals.

In a preferred embodiment a T7 ligand is described that selectively targets liver hepatocytes, wherein the T7 ligand is selected from the group comprising: a T7 phage, a T7 p17 protein, a fragment of the T7 p17 protein, a T7 p17 rod-domain, a peptide fragment of the p17 rod-domain, or a synthetic analog of this peptide. A T7 ligand is present as a protein determinant within the tail fiber protein p17 of a T7 phage clone. A preferred peptide fragment comprises a portion of the p17 rod domain and includes: Lys-Asn-Glu-Ser-Ser-Thr-Asn-Ala-Thr-Asn-Thr-Lys-Gln-Trp-Arg-Asp-Glu-Thr-Lys-Gly-Phe-Arg-Asp-Glu-Ala-Lys$_{211}$-Arg-Phe-Lys-Asn-Thr-Ala-Gly (SEQ ID 1). Modifications to the above mentioned T7 ligands, including amino acid substitutions, deletions or additions, that do not disrupt hepatocyte targeting are also T7 ligands. Synthetic analogs include both peptide based and non-peptide based molecules that structurally or functionally mimic the T7 ligand. Compounds that compete with a known T7 ligand for binding to hepatocytes are also considered T7 ligands. In a preferred embodiment, a T7 ligand may be modified, such as by addition of one or more functional groups, to facilitate attachment to other compounds.

In a preferred embodiment a T7 ligand can be used to deliver a cargo compound to hepatocytes. Attachment of the compound to a T7 ligand and injection of the conjugate into a vessel in a mammal results in delivery of the conjugate to hepatocytes. The T7 ligand can be attached through a covalent bond or through a non-covalent interaction to the cargo. The ligand can also be attached either directly or indirectly to the cargo. The T7 ligand can be attached to a cargo compound via a spacer. The cargo can be a biologically active compound such as a drug, protein or nucleic acid. The cargo can also be a carrier molecule or vehicle wherein the carrier molecule or vehicle, along with the ligand, facilitates delivery of a biologically active compound to hepatocytes. The cargo can be either particulate and soluble. The cargo can be a complex or it can be T7 phage. A complex can be a nucleic acid-containing or pharmaceutical-containing complex. A T7 phage can be made which contains a mammalian gene expression cassette. A biologically active compound can be attached to the T7 phage. In a preferred embodiment, the T7 ligand can be used to target viral and non-viral vectors to hepatocytes in vivo or in vitro. In a preferred embodiment, the T7 ligand can be used to deliver a therapeutic cargo to a hepatocyte in a mouse, rat, monkey or human.

In a preferred embodiment, a T7 ligand may be produced in bacteria or in animal cells or may be produced synthetically. The ligand may be modified to facilitate its attachment to other compounds. One type of modification includes the addition of a thiol, such as from a cysteine residue, on the peptide. This thiol can then be used to link the ligand to another compound though covalent attachment. The ligand can also be coupled to a cargo compound by attaching the ligand to one partner of a non-covalent coupling system such as biotin/streptavidin or antibody/epitope. The other partner is then linked to the cargo. This indirect method of attachment allows a modular design; for example, where a biotin-T7-ligand conjugate can be readily attached to any streptavidin-cargo conjugate. In another preferred embodiment, the T7 ligand may be made as a fusion or chimeric protein. Other coupling methods are also possible provided that the coupling does not interfere with the targeting function of the ligand. Many cross-linking reagents known in the art are available to link the ligand to a cargo compound.

In a preferred embodiment, the hepatocyte receptor for the T7 ligand and the internalization pathway for this ligand provide a therapeutically important pathway for targeting particles to the liver. This pathway efficiently internalizes complexes at least as large as the T7 phage, ~60 nm in diameter, into hepatocytes. The T7 ligand receptor is the component present on hepatocytes to which the T7 ligand binds. Ligands for other liver receptors such as the asialoglycoprotein receptor are frequently not specific to the liver or target Kupffer cells as well as hepatocytes. The T7 ligand pathway provides a means to decrease Kupffer cell uptake and still target particles to hepatocytes in the liver. Other natural or synthetic ligands which utilize the T7 receptor and internalization pathway may also be used.

In a preferred embodiment, we describe a process for intravascular delivery of a compound to hepatocytes comprising: conjugating a T7 ligand to the compound and inserting the conjugate, in a pharmaceutically acceptable buffer, into a vessel, wherein the T7 ligand targets the compound to hepatocytes. In a preferred embodiment, the process can be used to deliver a therapeutic compound to a hepatocyte in a mouse, rat, monkey, or human.

In a preferred embodiment, the described T7 ligand can be used in generating liver specific delivery systems. These systems can be used to effectively target compounds to hepatocytes. The delivery systems include attachment of the T7 ligand to a compound of interest, synthetic vector, viral vector or non-viral vector. The T7 ligand can thus be used in the generation of targeted drugs for the treatment of liver disease. The T7 ligand liver delivery system can be injected into a vessel or formulated to allow an oral delivery route.

In a preferred embodiment, the hepatocyte can be a primary or secondary cell which means that the cell has been maintained in culture for a relatively short time after being obtained from a mammal. The process may be used to deliver a biologically active compound to a mammalian hepatocyte that is ex vivo. The cell may then be re-implanted or transplanted into a mammal.

In a preferred embodiment, the hepatocyte can be a mammalian cell that is maintained in tissue culture such as cell lines that are immortalized or transformed. These include a number of cell lines—such as, but not limited to: HepG2 cells, Hepa cells, and the like—that can be obtained from American Type Culture Collection and other sources. The T7 ligand may also bind to other cell types such as 3T3 cells.

DETAILED DESCRIPTION

We have determined that a bacteriophage T7 clone containing a truncated coat p10 and a wild-type tail fiber protein p17 selectively localizes to hepatocytes when injected into a blood vessel in a mammal. Phage that contained certain missense mutations in the p17 gene did not target the liver. For instance, T7 phage carrying a Lysine to Glutamate mutation at position 211 in the p17 tail fiber protein, T7-$E_{211}$, do not target to liver hepatocytes. In contrast, within 30 min after injection into the blood stream, T7-$K_{211}$ phage accumulate in liver with an efficiency as high as ~75%. Analysis of the liver targeting determinant of T7 phage shows that it comprises a part of the α-helical coiled-coil rod domain of the phage tail fiber protein, p17. This determinant, by itself, predominantly localizes to hepatocytes after intravascular injection. Furthermore, the T7 ligand maintains its targeting properties when attached to other compounds. The T7 ligand can therefore be used to target compounds to hepatocytes.

Full-length p17 can be produced in bacteria and purified by affinity chromatography. It has been reported that purified p17 can spontaneously form trimers that are functionally equivalent to the phage tail fiber [Steven et al 1988; Studier 1969]. We now show that the purified protein retains the hepatocyte targeting function we have observed for the intact phage. Specifically, we show that purified p17-$K_{211}$ (wild-type) protein associates with hepatocytes when injected in vivo, while p17-$E_{211}$ (Lysine to Glutamate mutation at position 211) protein localizes mostly in sinusoidal areas. P17 protein is thus sufficient for hepatocyte targeting.

Figures 1, 2:
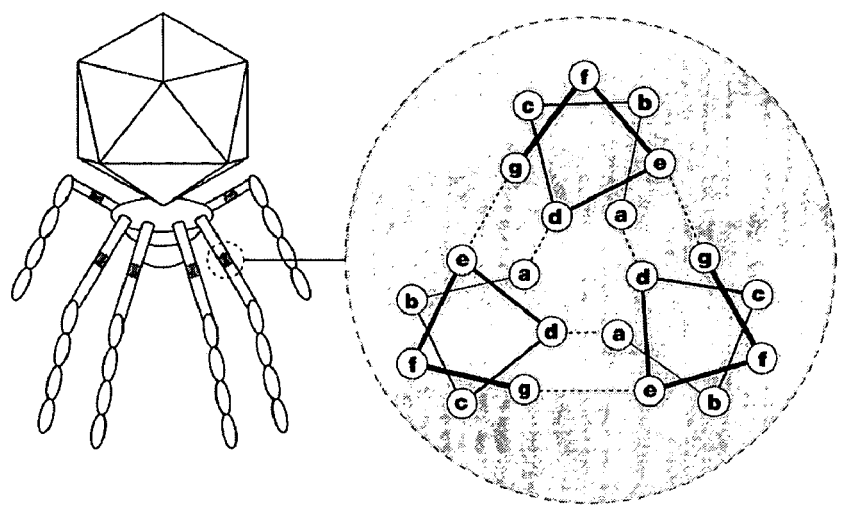
FIG. 1. Structural features of T7 phage. (A) Model of T7 phage. A region of the rod domain of the p17 protein is circled. (B) A cross-sectional view of the p17 triple-stranded coiled coil domain (rod domain) showing a single heptad repeat. The hydrophobic interactions between amino acid residues in a and d positions and electrostatic interactions between positive and negative residues in e and g positions are shown as dashed lines.
FIG. 2. Illustration of the components of a T7 ligand directed liver targeted delivery system.

Truncated p17-$K_{211}$ proteins, containing only amino acids 1–289, 150–553, or 150–289 (rod-domain alone) also retain hepatocyte targeting function. The $E_{211}$ mutation abolishes hepatocyte targeting function for each of these peptides. The central, rod-domain, portion of the p17 fiber protein—about 117 residues starting from Phenylalanine at position 151—is a triple-stranded α-helical coiled-coil domain that forms a rod-shaped structure 2 nm in diameter and 16.4 nm long in its native context (FIG. 1). The amino-terminus, residues 1–150, links the fiber to the tail-tube of the phage. The distal half of the fiber is made up of four globules in a rigid linear array. Four point mutations in the rod-domain are known to disrupt hepatocyte targeting. These mutations are: Lysine at position 211 to Glutamate, Arginine at position 207 to Leucine, Arginine at position 200 to Cysteine, and Arginine at position 200 to Serine in phages T7-$E_{211}$, T7-$L_{207}$, T7-$C_{200}$ and T7-$S_{200}$, respectively. These mutations occur within the rod-domain and occupy position b or e in the α-helical coiled-coil heptad repeat assignment for the protein (see FIG. 1B and Table 3). Because changes in the R groups at these positions can alter hepatocyte targeting, these positions are important for T7 ligand function.

We have made a number of synthetic peptides that have T7 ligand function. These peptides contain amino acid sequence similar to sequence found in the T7 phage p17 protein (Table 1A and SEQ ID 5). Synthetic peptides corresponding to amino acids 191–218, 190–218, 189–218, 188–218, 186–218 and 218–225 of the T7 phage p17 protein all have T7 ligand function. Peptides 186–218 and 186–225 exhibited more efficient hepatocyte targeting. We show that conservative amino acid substitutions—arginine to lysine or lysine to arginine—at residues 200 and 211 do not disrupt hepatocyte targeting of the T7 ligand. However, charge reversal substitution at position 211—lysine to glutamic acid—eliminates T7 ligand function (Table 1B). Multiple conservative lysine to arginine substitutions at positions 186, 211 and 214 or positions 197, 204, and 211 disrupt T7 ligand function, indicating that lysine(s) at position(s) 186, 197, 204, and/or 214 are important for peptide T7 ligand function. Three truncations, eliminating residues 186–203, 186–196, or 186–191 also resulted in loss of T7 ligand function. An aspartic acid-glutamic acid substitution at positions 215–216 is predicted to increase the propensity of the peptide to form an α-helical coiled coil structure and does not adversely affect T7 ligand function of the peptide. The inclusion of additional residues (amino acids 219–225 of p17) at the carboxy terminus also did not disrupt T7 ligand function. Table 1 summarizes permissible amino acid changes that do not disrupt hepatocyte targeting (Table 1a) and amino acid changes that disrupt hepatocyte targeting (Table 1b).

TABLE 1a

Functional Peptide T7 Ligands

KNESSTNATNTKQWRDETKGFRDEAKRFKNTAG - SEQ ID 1
KNESSTNATNTKQWRDETKGFRDEARRFKNTAG - SEQ ID 14
KNESSTNATNTKQWKDETKGFRDEAKRFKNTAG - SEQ ID 15
KNESSTNATNTKQWRDETKGFRDEAKRFKNTAGQYATSG - SEQ ID 16
KNESSTNATNTKQWRDETKGFRDEAKRFKDEAG - SEQ ID 17
        TNATNTKQWRDETKGFRDEAKRFKNTAG - SEQ ID 18
         STNATNTKQWRDETKGFRDEAKRFKNTAG - SEQ ID 19
        SSTNATNTKQWRDETKGFRDEAKRFKNTAG - SEQ ID 20
        ESSTNATNTKQWRDETKGFRDEAKRFKNTAG - SEQ ID 21
KNESSTNATNTKQWRDETKGFRDEADly²RFKNTAG - SEQ ID 22
KNESSTNATNTKQWRDETKGFRDEAO³RFKNTAG - SEQ ID 23
KNESSTNATNTKQWRDETKGFRDEAKRF - SEQ ID 24

[1] amino acids 186–218 of the T7 phage p17 protein
[2] Dly = dimethyl lysine
[3] O = ornithine TABLE 1b Amino acid substitutions/deletions that disrupt hepatocyte targeting of Peptide T7 Ligands.

KNESSTNATNTKQWRDETKGFRDEAERFKNTAG - SEQ ID 25
RNESSTNATNTKQWRDETKGFRDEARRFRNTAG - SEQ ID 26
KNESSTNATNTRQWRDETRGFRDEARRFKNTAG - SEQ ID 27
KNESSTNATNTKQWRDETKGFRDEA - SEQ ID 28
    SSTNATNTKQWRDETKGFRDEAKRF - SEQ ID 29
KNESSTNATNTKQWRDETKGFRDEAKRF - SEQ ID 30
            KGFRDEAKRFKNTAG - SEQ ID 31
        KQWRDETKGFRDEAK

Modification of the particles, by addition of functional groups such as the T7 ligand, can be made either before particle formation, by modification of the components, or after particle formation. Molecules such as PEG can be incorporated onto the delivery vehicle to increase stability, decrease interaction with serum constituents, or provide a spacer between the particle and the T7 ligand. Attachment of the T7 ligand can be via direct chemical conjugation or can be indirect.

The T7 ligand may be produced recombinantly in bacteria or animal cells or may be produced synthetically in a cell-free system. The ligand may be modified to facilitate its attachment to other compounds. One modification includes the inclusion of a thiol, such as from a cysteine residue, onto either the amino or carboxyl end of the peptide. This unique thiol can then be used to link the ligand to another compound though covalent attachment. Other functional or reactive groups may also be attached to the T7 ligand to facilitate attachment to another compound. The ligand can also be coupled indirectly to a cargo compound by attaching the ligand to one partner of a non-covalent coupling system such as biotin/streptavidin or epitope/antibody. The other partner is then linked to the cargo. This indirect method allows a modular design; for example, where a biotin-ligand conjugate can be readily attached to any streptavidin-cargo conjugate.

The genetic attachment of a T7 ligand to a recombinant therapeutic protein represents a method to attach the T7 ligand to a protein or peptide, i.e., the ligand can be produced as a fusion or chimeric protein. The T7 ligand may also be incorporated into viruses, such as adenovirus or retroviruses. The coiled-coil structure of the p17 protein rod domain, including the T7 ligand, may be incorporated into the triple-helix structure present in coat proteins of some viruses.

The T7 phage p17 hepatocyte targeting ligand can also be attached to a cargo compound via a spacer molecule such a PEG or chemically similar molecule. The PEG may shield the rod domain from nonproductive interactions with the cargo. Presenting the targeting ligand at the end of a PEG spacer may increase its accessibility to cell surface receptors. Other spacers or linkers include, but are not limited to, polysaccharides, dextrans, polymers, proteins, and acyl groups.

Other coupling methods are also possible provided that the coupling does not interfere with the targeting function of the p17 hepatocyte targeting function. Many cross-linking reagents are known in the art and available to link the ligand to a target compound.

A ligand is a compound that enhances binding to a cell in a selective manner. A ligand may increase binding of a compound to the cell surface and/or its association with an intracellular compartment. A ligand can be, but is not limited to: a protein, peptide, lipid, steroid, sugar, carbohydrate, or synthetic compound. The ligand may bind a target within the cell membrane, on the cell membrane or near a cell. Binding of a ligand to a receptor may initiate endocytosis. A ligand can modify a compound and can direct it to a cell type or location (such as tissue) either in culture or in a whole organism.

The general scheme for a liver targeted delivery system comprises the diagram shown in FIG. 2, wherein the system minimally consists of the T7 ligand and the cargo. The T7 ligand may be linked to the cargo by one or more additional elements such as is shown in the diagram. The attachment chemistry and linker may further include a variety of functional groups.

Functional group. Functional groups include cell targeting signals, nuclear localization signals, compounds that enhance release of contents from endosomes or other intracellular vesicles (releasing signals), reactive groups, and other compounds that alter the behavior or interactions of the compound or complex to which they are attached.

Another functional group comprises compounds, such as polyethylene glycol, that decrease interactions between molecules and themselves and with other molecules. Such groups are useful in limiting interactions such as between serum factors and the molecule or complex to be delivered.

A linkage is an attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyether, polyamine, thiol, thio ether, thioester, phosphorous containing, and heterocyclic. The linkage may or may not contain one or more labile bonds. A spacer group can provide a means to increase the distance between the ligand and the cargo, shield the ligand from the cargo, provide attachment for multiple cargo compounds or multiple ligands, or provide better presentation or orientation of the ligand. An example of a spacer is a poly(ethyleneglycol), PEG, or similar molecule. The PEG would shield the rod domain from interaction with the cargo. Presenting the targeting ligand at the end of a PEG spacer may increase its accessibility to cell surface receptors.

Cargo may be selected from the list comprising: HMG CoA reductase inhibitors, [statins, statin class drugs, atorvastatin (LIPITOR®), cerivastatin (BAYCOL®), fluvastatin (LASCOL®), lovastatin (MEVACOR®), pravastatin (PREVACHOL®), simvastatin (ZOCOR®), second generation statins, rosuvastatin (CRESTOR®, ZD 4522)], interferons [interferon class drugs, modified interferons, pegylated interferon, pegylated interferon alfa-2b, PEG-INTRON®, PEGASYS®, VIRAGERON®], cholesterol absorption inhibitors [ZETIA®, ezetimibe, plant stanols], bile acid absorption inhibitors, bile acid sequestrants, anti-fungal drugs [Cytochrome P450 inhibitors, itraconazole (SPORONOX®), erythromycin], triglyceride lowering drugs [fibrates, fibric acid derivatives, gemfibrozil, bezafibrate], antiviral drugs [anti-hepatitis drugs, hepatitis therapeutics, histamine dihydrochloride, CEPLENE® (MAXAMINE®), HEPSERA®, adefovir dipivoxil 5-iodo-2'-deoxyuridine, Amantadine, SYMMETREL®], nucleotide/nucleoside analogs [nucleosides, Ribavarin, REBETRON®, REBETOL®, Lamivudine (ZEFFIX®, EPIVIR®, 3TC®), zidovudine (RETROVIR®, azidothymidine, AZT®, or ZDV)], anticholelithics/gallstone therapeutics [ursodeoxycholic acid (Ursodiol, ursodeoxycholic acid (UDCA), Actigal, Chenodiol (Chenix)], antioxidants [histamine type-2 receptor agonists, Maxamime, N-acetylcysteine, vitamin E, alpha lipoic acid (thioctic acid), silymarin, selenium], protease inhibitors, interleukins, glycyrrhizin, alcohol induced cirrhosis treatments [propylthiouracil, colchicines, thromboxanes, polyenylphosphatidylcholine], anti-rejection drugs [CellCept (mycophenolatemofetil), Imuran (azathioprine (AZA)), cyclophosphamide, Deltasone, Orasone (Prednisone), Neoral, Sandimmune (cyclosporines), OKT3, Orthoclone OKT3, Prograf (FK506, tacrolimus), prostaglandins, Rapamune (Sirolimus), Muromonab CD3 or OKT3 (Orthoclone), Thymoglobulin (Anti-Thymocyte Globulin), IL-2-Receptor Antagonist Antibodies], anticancer therapeutics [MTC-DOX, doxorubicin, 5-fluorouracil (5 FU), Leucovorin, Mitomycin C, CPT-1 1, 3-bromopyruvate, T67, cancer drugs that typically are useful in other tissues may be made useful in liver cancer by redirecting their localization], MRI contrast agents [heavy elements (Gd, Mn, Dy) Extracellular agents (Gd HP-DO3A, Gd DTPA, and Gd DTPA-BMA), Gadolinium chelates (Gd BOPTA and Gd EOB-DTPA), particulate agents (AMI-25); attachment of the contrast agent to a T7 ligand may allow lower dosage and less invasive administration techniques], particulate imaging agents [scintography agents (particles with 99 mTc, 111In isotopes attached), particles for positron emission tomography, iodine-containing and other particles for x-ray (CT) tomography], viruses and viral vectors [adenovirus, gutted adenovirus, adeno-associated virus, retroviruses, lentiviruses], non-viral vectors, [complexes, liposomes, polymers, polyplexes, lipopolyplexes, micelles, transfection reagents], biologically active compounds, nucleic acids and RNA function inhibitors.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. Biologically active compounds may be selected from the group comprising: pharmaceuticals, proteins, peptides, polypeptides, hormones, cytokines, antigens, viruses, oligonucleotides, and nucleic acids.

The term nucleic acid, or polynucleotide, is a term of art that refers to a polymer containing at least two nucleotides. Nucleotides are the monomeric units of nucleic acid polymers. Polynucleotides with less than 120 monomeric units are often called oligonucleotides.

Natural nucleic acids have a deoxyribose- or ribose-phosphate backbone while artificial polynucleotides are polymerized in vitro and contain the same or similar bases but may contain other types of backbones. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The term polynucleotide includes deoxyribonucleic acid (DNA) and ribonucleic acid (RNA). Natural polynucleotides have a ribose-phosphate backbone. An artificial or synthetic polynucleotide is any polynucleotide that is polymerized in vitro or in a cell free system and contains the same or similar bases but may contain a backbone of a type other than the natural ribose-phosphate backbone.

DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An antisense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15–50 base pairs and preferably 21–25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA. In addition, DNA and RNA may be single, double, triple, or quadruple stranded.

A nucleic acid can be delivered to a cell to express an exogenous nucleotide sequence, to inhibit, eliminate, augment, or alter expression of an endogenous nucleotide sequence, or to affect a specific physiological characteristic not naturally associated with the cell. Nucleic acids may contain an expression cassette coded to express a whole or partial protein, or RNA. An expression cassette refers to a natural or recombinantly produced nucleic acid that is capable of expressing a gene(s). The term recombinant as used herein refers to a nucleic acid molecule that is comprised of segments of polynucleotide joined together by means of molecular biological techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences.

RNA function inhibitor. A RNA function inhibitor ("inhibitor") comprises any nucleic acid or nucleic acid analog containing a sequence ("inhibiting sequence") whose presence or expression in a cell causes the degradation of or inhibits the function or translation of a specific cellular RNA, usually a mRNA, in a sequence-specific manner. Inhibition of RNA can thus effectively inhibit expression of a gene from which the RNA is transcribed. Inhibitors are selected from the group comprising: siRNA, interfering RNA or RNAi, dsRNA, RNA Polymerase III transcribed DNAs, ribozymes, and antisense nucleic acid, which may be RNA, DNA, or artificial nucleic acid. SiRNA comprises a double stranded structure typically containing 15–50 base pairs and preferably 21–25 base pairs and having a nucleotide sequence identical or nearly identical to an expressed target gene or RNA within the cell. Antisense polynucleotides include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded.

Protein (or peptide) refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein (e.g., low density lipoprotein receptor). Therapeutic proteins that stay within the cell ("intracellular proteins") can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

A non-viral vector is defined as a vector that is not assembled within an eukaryotic cell including protein and polymer complexes (polyplexes), lipids and liposomes (lipoplexes), combinations of polymers and lipids (lipopolyplexes), micelles, and multilayered and recharged particles. Non-viral vectors may be used to deliver nucleic acid, drugs or therapeutic agents to cells A polymer is a molecule built up by repetitive bonding together of smaller units called monomers. Small polymer having 2 to about 80 monomers can be called oligomers. The polymer can be linear, branched network, star, comb, or ladder type. The polymer can be a homopolymer in which a single monomer is used or can be copolymer in which two or more monomers are used. Types of copolymers include alternating, random, block and graft. The main chain of a polymer is composed of the atoms whose bonds are required for propagation of polymer length. The side chain of a polymer is composed of the atoms whose bonds are not required for propagation of polymer length. To those skilled in the art, there are several categories of polymerization processes that can be utilized in the described process. The polymerization can be chain or step. This classification description is more often used than the previous terminology of addition and condensation polymerization. Template polymerization can be used to form polymers from daughter polymers.

A liposome is an artificial microscopic vesicle comprising amphipathic molecules, used to convey vaccines, drugs, enzymes, nucleic acid, or other substances to target cells or organs.

A lipid is any of a diverse group of organic compounds that are insoluble in water, but soluble in organic solvents such as chloroform and benzene. Lipids contain both hydrophobic and hydrophilic sections. A lipids is meant to include complex lipids, simple lipids, and synthetic lipids.

A polyplex is complex consisting of two or more ionic polymers or proteins, used to convey vaccines, drugs, enzymes, nucleic acid, or other substances to target cells or organs.

A lipopolyplex is a complex consisting of one or more amphipathic molecules and one or more ionic polymers or proteins, used to convey vaccines, drugs, enzymes, nucleic acid, or other substances to target cells or organs.

A transfection reagent is a compound or compounds that bind(s) to or complex(es) with oligonucleotides and polynucleotides, and mediates their entry into cells. The transfection reagent also mediates the binding and internalization of oligonucleotides and polynucleotides into cells. Examples of transfection reagents include, but are not limited to, cationic lipids and liposomes, polyamines, calcium phosphate precipitates, histone proteins, polyethylenimine, and polylysine complexes. It has been shown that cationic proteins like histones and protamines, or synthetic cationic polymers like polylysine, polyarginine, polyornithine, DEAE dextran, polybrene, and polyethylenimine may be effective intracellular delivery agents, while small polycations like spermine are ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via cell targeting signals that bind to receptors on or in the cell. For example, cationic liposomes or polylysine complexes have net positive charges that enable them to bind to DNA or RNA. Polyethylenimine, which facilitates gene transfer without additional treatments, probably disrupts endosomal function itself.

Two molecules are combined, to form a complex through a process called complexation or complex formation, if the are in contact with one another through non-covalent interactions such as electrostatic interactions, hydrogen bonding interactions, and hydrophobic interactions.

A covalent bond is a chemical bond formed by the sharing of one or more electrons, especially pairs of electrons, between atoms.

In a non-covalent bond, the atoms interacting do not each contribute an electron to form an electron pair bond (a covalent bond). Examples of non covalent bonds include salts such as sodium chloride and potassium chloride. Non-covalent bonds also include the interactions between crown ethers and a cation (for example 18-crown-6 and potassium), hydrogen bonds, and hydrophobic interactions.

A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. Labile also means cleavable.

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-labile linkages and bonds. pH-labile refers to the selective breakage of a covalent bond under acidic conditions (pH<7). That is, the pH-labile bond may be broken under acidic conditions in the presence of other covalent bonds without their breakage. Disubstituted maleic anhydrides can be used to provide pH-labile linkages. The covalent bond formed by reaction between an amine on a compound of interest and the anhydride is readily cleaved at acidic pH. Thus, maleic anhydride derivatives can be reversibly attached to amine-containing compounds. 2-propionic-3-methylmaleic anhydride (CDM) is a carboxylic acid-containing derivative of the disubstituted maleic anhydride. CDM-Thioester adds a thioester reactive group to the carboxyl of CDM. Disubstituted maleic anhydrides can be used to modify or add functional groups to amine containing compounds or they may be used as crosslinkers.

Reactive groups are capable of forming either an ionic or a covalent bond with another compound. Examples of reactive groups include nucleophiles and electophiles. Reactive groups that form covalent bonds may be selected from the group comprising: isothiocyanate, isocyanate, acyl azide, acid halide, O-acyl urea, N-hydroxysuccinimide esters, succinimide esters, thioesters, amide, urea, sulfonyl chloride, aldehyde, ketone, ether, epoxide, carbonate, alkyl halide, imidoester, carboxylate, alkylphosphate, arylhalides (e.g. difluoro-dinitrobenzene), and anhydrides.

Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule.

Bifunctional molecules, commonly referred to as crosslinkers, are used to connect two molecules together, i.e. form a linkage between two molecules. Bifunctional molecules can contain homo or heterobifunctionality.

EXAMPLES

1. T7 Phage Uptake by Liver in Mouse: T7-$E_{211}$ and T7-$K_{211}$ phage, both containing a truncated p10 coat protein ending in sequence VVFQ343, were grown, isolated and titered as previously described [Sokoloff et al. 2000]. Mice were anesthetized by an intramuscular injection of ketamine (80–100 mg/kg) and xylazine (2 mg/kg). $10^9$–$10^{11}$ pfu (plaque-forming units) of T7 phage in 1 ml of PBS were injected into the tail vein over 60 sec. After 60 min, 10 units of heparin in 0.5 ml of PBS were injected into the tail vein, and the liver was perfused through the portal vein, with the right atrium cut, with PBS containing 2 unit/ml heparin. Perfused livers were removed and homogenized in PBS containing 2% Triton X-100 and 1M NaCl. The amount of liver-associated phage was evaluated by a plaque forming assay (Table 2.) [Sokoloff et al. 2000].

TABLE 2

T7 phage uptake by liver.

| Phage type | p17 tail fiber sequence | % live phage in liver[1] | Phage in Hepatocytes | 5 min | 30 min |
|---|---|---|---|---|---|
| T7-$E_{211}$ | $R_{207}DEAE_{211}RF$ | 3.7 ± 1.66 | # particles/cell | 1 . 5 | 3–7 |
| | | | percent of cells | 20% | 50% |
| T7-$K_{211}$ | $R_{207}DEAK_{211}RF$ | 74.8 ± 5.70 | # particles/cell | 50–250 | 500–2000 |
| | | | percent of cells | 100% | 100% |

[1]60 min after injection, mean and standard deviation for n = 6 mice

Approximately 75% of liver-sequestered phage at 60 min after infection was infectious, thereby suggesting that the phage observed in hepatocytes was largely represented by intact phage particles rather than degraded phage material.

Two additional techniques, Percoll gradient and FACS, were used to determine the cellular distribution of infectious phage in liver. Liver cells were isolated by collagenase-dispase (Life Technologies) digestion of liver tissue and either purified by Percoll gradient centrifugation according to Life Technologies' protocol (No. 3736), or stained with propidium iodide and sorted by FACS according to chromosome ploidy [Weglarz et al. 2000]. In both cases, liver cells were fractionated into hepatocytes and NPCs, and infectious phage was measured in the separated cell populations. The amount of infectious phage associated with the hepatocyte-enriched cell fraction isolated by Percoll gradient centrifugation was ~90 times higher for phage T7-$K_{211}$ than for phage T7-$E_{211}$ (data not shown). The FACS sorting of liver cells into diploid cells, including both NPCs and hepatocytes, and tetraploid cells, containing almost exclusively hepatocytes [Severin et al. 1984], showed that a single tetraploid cell contained, on average, approximately 2.5 times more T7-$K_{211}$ particles than a single diploid cell (data not shown).

2. Localization of T7 phage targeted to liver: The association of phage sequestered by liver with hepatocytes and non-parenchymal cells (NPCs; Kupffer, endothelial cells and Ito cells) was analyzed by immunohistochemistry. $10^{11}$ pfu of T7 phage in 400 μl of PBS were injected into the tail vein of male ICR mice (18–22 g, Charles River Lab) over 30–40 seconds. The percentage of phage-containing hepatocytes was determined at 5 min and 30 min after phage injection. Livers were harvested under isoflurane inhalation anesthesia, and the animals were euthanized by an overdose of isoflurane. A ~5 mm thick section of liver tissue was excised from the left lateral lobe and snap-frozen in O.C.T. compound. Liver sections (5–7 μm thick) were prepared using a Microm HM 505 N cryostat (Carl Zeiss), mounted on Superfrost Plus Fisher slides and air dried overnight. Before immunostaining, the sections were fixed in 4% formaldehyde for 20 min, washed 3 times with PBS and blocked with 10% normal donkey serum in PBS for 30 min. All antibody solutions were prepared in PBS containing 2 mg/ml BSA, and all antibody incubations were done at room temperature for 60 min. Liver sections were incubated with rabbit anti-T7 antibody (1:2500), washed 3 times with PBS and incubated with 3.5 μg/ml Cy3-conjugated donkey anti-rabbit antibody (Jackson Immuno-Research). Sections were washed 3 times with PBS and counterstained for 20 min with 13 nM ToPro-3 (Molecular Probes) to visualize nuclei and with 16.5 nM Alexa 488-phalloidin (Molecular Probes) to visualize actin filaments near cellular and bile capillary membranes. Counterstained sections were rinsed 3 times with PBS, sealed in Vectorshield medium (Vector Laboratories) and analyzed under a confocal Zeiss LSM 510 microscope (Zeiss). Cy3 fluorescence ($\lambda_{ex}$ 543 nm) was detected by using a 560–615 nm BP filter. Alexa 488-phalloidin ($\lambda_{ex}$ 488 nm) and To-Pro-3 ($\lambda_{ex}$ 633 nm) were detected by using 505–550 nm BP and 650 nm LP filters, respectively. Unless specified otherwise, images were reconstructed as a flattened projection of a stack of eight 0.4 μm optical sections.

The amount of intracellular material reactive with anti-T7 antibody was quantitated as follows. Five randomly chosen cells in each group were examined in reconstructed images (3 μm thick) acquired at using a 63× objective. At this magnification, the smallest "phage particle" appeared as a colored pixel. The average amount of phage in an individual hepatocyte was estimated as a number of stained pixels normalized to the intensity of staining. The number of bright pixels was multiplied by 4, the number of pixels with the intermediate brightness was multiplied by 2 and the number of weak pixels was multiplied by 1.

Figure 3:
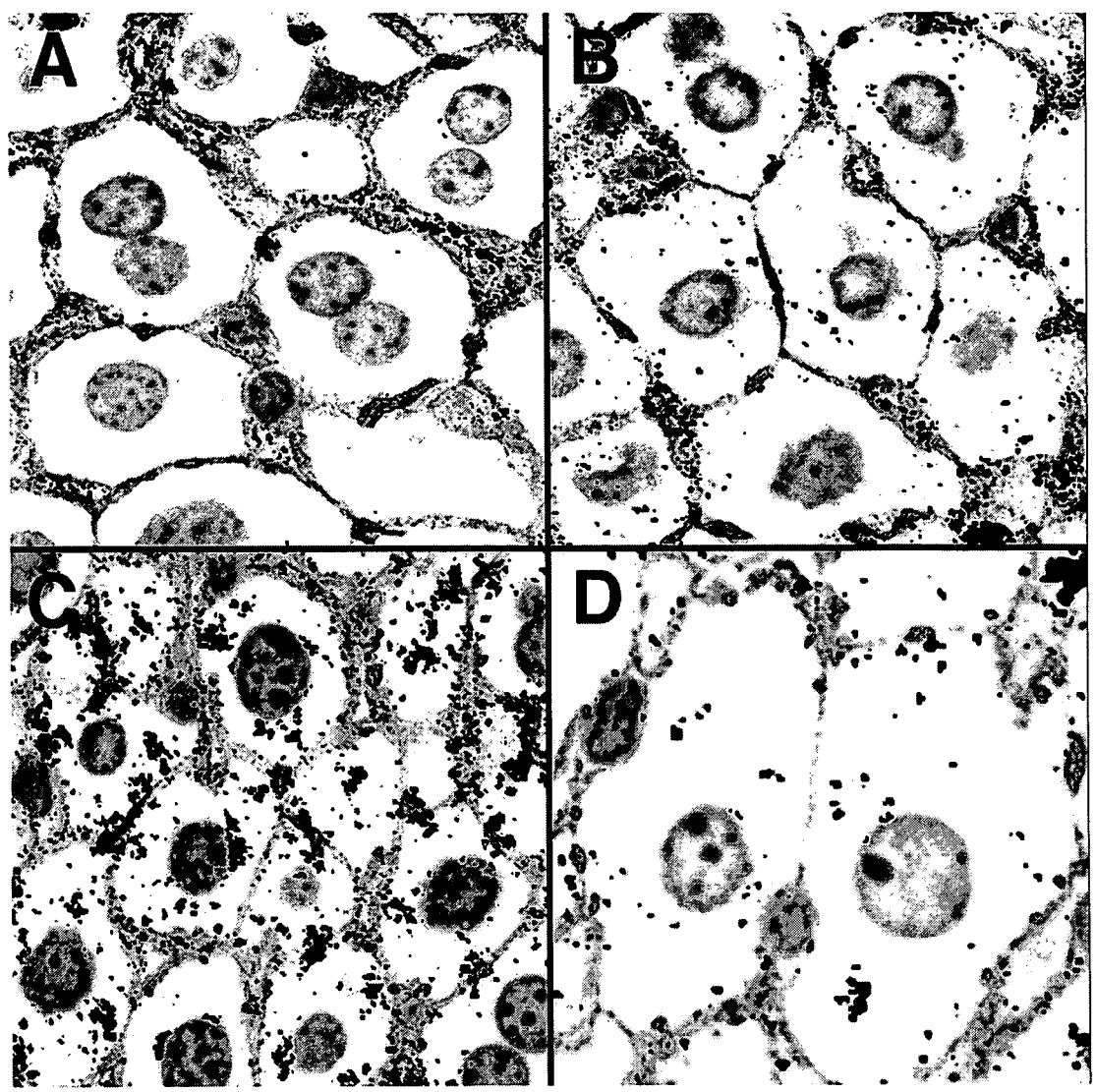
FIG. 3. Immunohistochemical localization of phage in mouse liver. $10^{11}$ T7 phage was injected into mice through the tail vein. 5 or 30 min after injection, the livers were removed, sectioned and stained for T7 phage. Phage is seen in black; nuclei and F-actin in gray. T7-$E_{211}$ at 30 min after injection (A). T7-$K_{211}$ at 5 min after injection (B) or at 30 min after injection (C, D). A–C are confocal optical sections (8) merged into a single image. D shows a single confocal optical section.

Immunohistochemical staining using anti-phage antibodies showed that phage T7-$E_{211}$ was present in liver almost exclusively in sinusoidal areas occupied by NPCs and blood (FIG. 3A and Table 2). In contrast, phage T7-$K_{211}$ was largely associated with hepatocytes (FIGS. 3B–D and Table 2). A substantial amount of phage T7-$K_{211}$ was associated with every hepatocyte as early as 5 min after injection (FIG. 3B and Table 2). A portion of this phage was inside hepatocytes. The amount of phage inside hepatocytes significantly increased by 30 min after injection (FIG. 3C and Table 2). The amounts of T7-$E_{211}$ and T7-$K_{211}$ phage present in sinusoidal areas at 30 min after injection were similar (FIGS. 3A and 3C).

Pre-injection of mice with 1 mg of asialofetuin did not noticeably decrease the amount of T7-$K_{211}$ phage that accumulated in hepatocytes (data not shown), suggesting that the ASGPr was not involved in phage uptake.

Three other mutant T7 phage were injected into mice and analyzed as above. These phage carried the following missense mutations in gene 17: Arginine to Leucine at position 207, Arginine to Cysteine at position 200, and Arginine to Serine at position 200. These mutations occur within the rod domain and occupy position b or e in the α-helical coiled-coil heptad repeat assignment for the protein. Each of these mutations disrupted the hepatocyte targeting of T7 phage (Table 3.).

TABLE 3

Effect of mutations in p17 on hepatocyte targeting of T7 phage.

| Phage Type | Liver targeting | p17 peptide sequence (residues 200–213)* | | | | | |
|---|---|---|---|---|---|---|---|
| | | e | f | g | a | b | d |
| $K_{211}$ | + | R | D | E | A | $K_{211}$ | R | F |
| $E_{211}$ | − | R | D | E | A | $E_{211}$ | R | F |
| $L_{207}$ | − | $L_{207}$ | D | E | A | K | R | F |
| $C_{200}$ | − | $C_{200}$ | D | E | T | K | G | F |
| $S_{200}$ | − | $S_{200}$ | D | E | T | K | G | F |

*The predicted positions of amino acid residues in the coiled-coil heptad repeats are shown with letters a through g (FIG. 1B).

3. Liver targeting of p17 Proteins: The DNA fragment containing the full-length gene 17 coding region (wild-type) was generated by PCR amplification of the cloned gene 17 using forward, 5'-aaggaggtCATATGgctaacgta-attaaaaccg-3' (SEQ ID 2), and reverse primers, 5'-gattGGATCCttactcgt-tctccaccatgattgcattag-3' (SEQ ID 3), containing Nde I and BamH I sites, respectively. The resultant PCR fragment was gel purified and subcloned into the pET28b plasmid (Novagen) in frame with the N-terminal His Tag coding sequence. The p17 gene from T7-$E_{211}$ was cloned in the same fashion, using phage T7-$E_{211}$ genomic DNA as a template. The rod domain (residues 150–289) [Steven et al 1988], the rod and amino-terminal domains (residues 1–289), and the rod and carboxy-terminal domains (residues 150–553) were cloned similarly.

The predicted amino acid sequence of the full length p17 protein, SEQ ID 4, is: <u>MGSSHHHHHHSSGLVPRGSH</u> MANVIKTVLTYQLDGSNRDFNIPFEYLARKFVVVTLI GVDRKVLTINTDYRFATRTTISLTKAWGPADGYTTIE LRRVTSTTDRLVDFTDGSILRAYDLNVAQIQTMHVAE EARDLTTDTIGVNNDGHLDARGRRIVNLANAVDDR DAVPFGQLKTMNQNSWQARNEALQFRNEAETFRN QAEGFKNESSTNATNTKQWRDETKGFRDEAKRFKN TAGQYATSAGNSASAAHQSEVNAENSATASAN SAHL AEQQADRAE READKLENYNGLAGAIDKVDGTNVY-WKGNIHANGRLYMTTNGFDCGQYQQFFGGVTNRY MEWGDENGWLMYVQRREWTTAIGGNIQLVVNGQI ITQGGAMTGQLKLQNGHVLQLESASDKAHYILSKD GNRNNWYIGRGSDNNNDCTFHSYVHGTTLTLKQDY AVVNKHFHVGQAVVATDGNIQGTKWGGKW LDAYL-RDSFVAKSKAWTQVWSGSAGGGVSVTVSQDLRFRN IWIK CANNSWNFFRTGPDGIYFIASDGGWL RFQIH-SNGLGFKNIADSRSVPNAIMVENE. The underlined sequence represents His tag sequence used in the purification of the protein.

The predicted amino acid sequence of the 150–289 rod domain peptide, SEQ ID 5, is: <u>MGSSHHHHHHSGLVPRGSH</u>PFGQLKTMNQNSWQ ARNEALQFRNEAETFRNQAEGFKNESSTNATNT KQWRDETKGFRDEAKRFKNTAGQYATSAGNSAAH QSEVNAENSATASANSAHLAEQQADRAEREADKLE NNGLAGAIDKVDGTNVYWKGN.The underlined sequence represents His tag sequence used in the purification of the protein.

The predicted amino acid sequence of the 1–289 peptide, SEQ ID 6, is: <u>MGSSHHHHHHSSGLVPRGSH</u> MANVIK-TVLTYQLDGSNRDFNIPFEYLARKFVVVTLI GVDRK VLTINTDYRFATRTTISLTKAWGPADGYTTIELRRVTS TTDRLVDFTDGSILRAYDLNVAQIQTMHVAEEARDL
TTDTIGVNNDGHLDARGRRIVNLANAVDDRDAVPF
QLKTMNQNSWQARNEALQFRNEAETFRNQAEGFK
NESSTNATNTKQWRDETKGFRDEAKRFKNTAGQYA
TSAGNSASAAHQSEVNAENSATASANSAHLAEQQA
DRAEREADKLENYNGLAGAIDKVDGTNVYWKGN.
The underlined sequence represents His tag sequence used in the purification of the protein.

The predicted amino acid sequence of the 150–553 peptide, SEQ ID 7, is: <u>MGSSHHHHHHSSGLVPRGSH</u> PFGQLKTMNQNSWQARNEALQFRNEAETFRNQAEG FKNESSTNATNTKQWRDETKGFRDEAKRFKNTAGQ YATSAGNSASAAHQSEVNAENSATASANSAHLAEQQ ADRAEREADKLENYNGLAGAIDKVDGTNVYWKGN IHANGRLYMTTNGFDCGQYQQFFGGVTNRYSVME WGDENGWLMYVQRREWTTAIGGNIQLVVNGQIITQ GGAMTGQLKLQNGHVLQLESASDKAHYILSKDGNR NNWYIGRGSDNNNDCTFHSYVHGTTLTLKQDYAVV NKHFHVGQAVVATDGNIQGTKWGGKWLDAY LRDS-FVAKSKAWTQVWSGSAGGGVSVTVSQDLRFRNIWI CANNSWNFFRTGPDGI YFIASDGGWLRFQIHSNGLG-FKNIADSRSVPNAIMVENE. The underlined sequence represents His tag sequence used in the purification of the protein.

Figure 4:
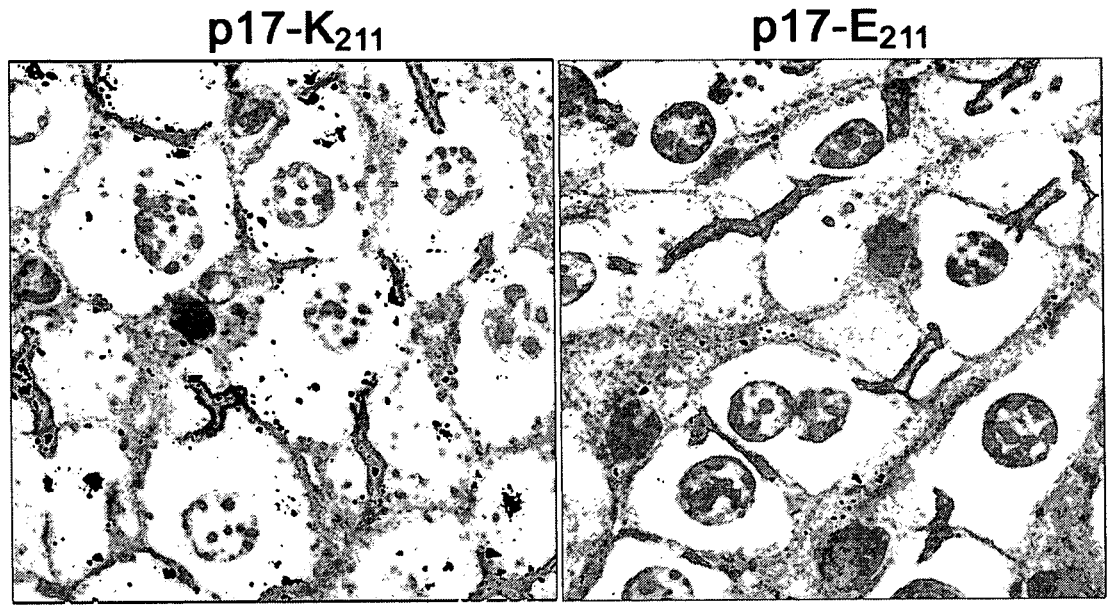
FIG. 4. Hepatocyte targeting by cloned p17 proteins. Bacterially expressed p17-$K_{211}$ or p17-$E_{211}$ was injected into mice through the tail vein. After 15 min, the livers were removed, sectioned and immunohistochemically stained for p17. p17 is seen in black; nuclei and F-actin in gray.

The liver targeting by cloned p17 proteins was tested by injecting 5 μg of each peptide in 250 μl of PBS into mice via tail vein. Fifteen min after the injection, livers were removed, sectioned, immunostained and examined for the presence of p17 by confocal microscopy as described above for intact phage (FIG. 4). Localization of the p17-$K_{211}$ rod domain (aa 150–289), p17-$K_{211}$ amino-terminal+rod domain (aa 1–289), and p17-$K_{211}$ rod+carboxy-terminal domain (aa 150–553) were similar to p17-$K_{211}$.

Figure 5:
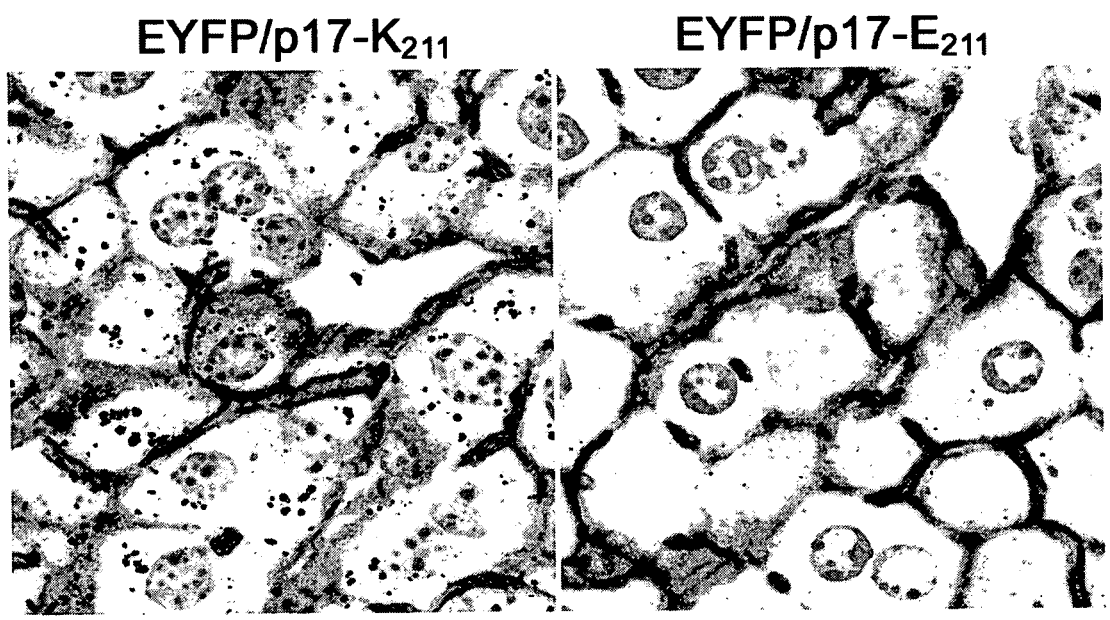
FIG. 5. Targeting of EYFP protein to hepatocytes with p17-$K_{211}$. EYFP-p17-$K_{211}$ or EYFP-p17-$E_{211}$ was injected into mice through the tail vein. After 15 min, the livers were removed, sectioned and analyzed for EYFP fluorescence. EYFP is seen as black spots. Cell nuclei and F-actin are gray.

4. The T7 ligand targets yellow fluorescent protein to hepatocytes in vivo: The utility of the hepatocyte targeting p17 determinant for heterologous cargo delivery was evaluated by genetically fusing the whole-length p17 to Enhanced Yellow Fluorescent Protein (EYFP). The coding region of EYFP-Nuc from the pEYFP-Nuc plasmid (Clontech) was amplified by using 5'-cggtcgccCATATGgtgagcaagggc-gagga-3' (SEQ ID 8) and 5'-gattatgatCATATGtctagatccggtg-gatcctac-3' (SEQ ID 9) primers with incorporated NdeI sites. The PCR product was gel purified, digested with NdeI and ligated into the NdeI digested pET28b plasmid coding either for the wild-type p17-$K_{211}$ or p17-$E_{211}$ full-length proteins. Recombinant fusion proteins were prepared using Rosetta® DE3 E.coli host cells (Novagen) and purified using a Ni-NTA Agarose (Qiagen) affinity chromatography. The liver targeting of EYFP/p17 fusion proteins was tested by injecting 75 μg of protein in 250 μl PBS into mice via tail vein. Animals were sacrificed 15 min after injections and livers were gently perfused with PBS. Liver sections were prepared as above and counterstained with ToPro-3 and Alexa 546-Phalloidin as above. The sections were analyzed by confocal microscopy, detecting EYFP ($\lambda_{ex}$ 488) by using a 505–550 BP filter and Alexa 546 ($\lambda_{ex}$ 543) by using a 560–615 BP filter. All images represented a flattened projection of a stack of twelve 0.4 μm sections. EYFP/p17-$K_{211}$ fusion protein accumulated in hepatocytes, while the EYFP/p17-$E_{211}$ fusion protein was mostly observed in the sinusoidal areas (FIG. 5).

Figure 6:
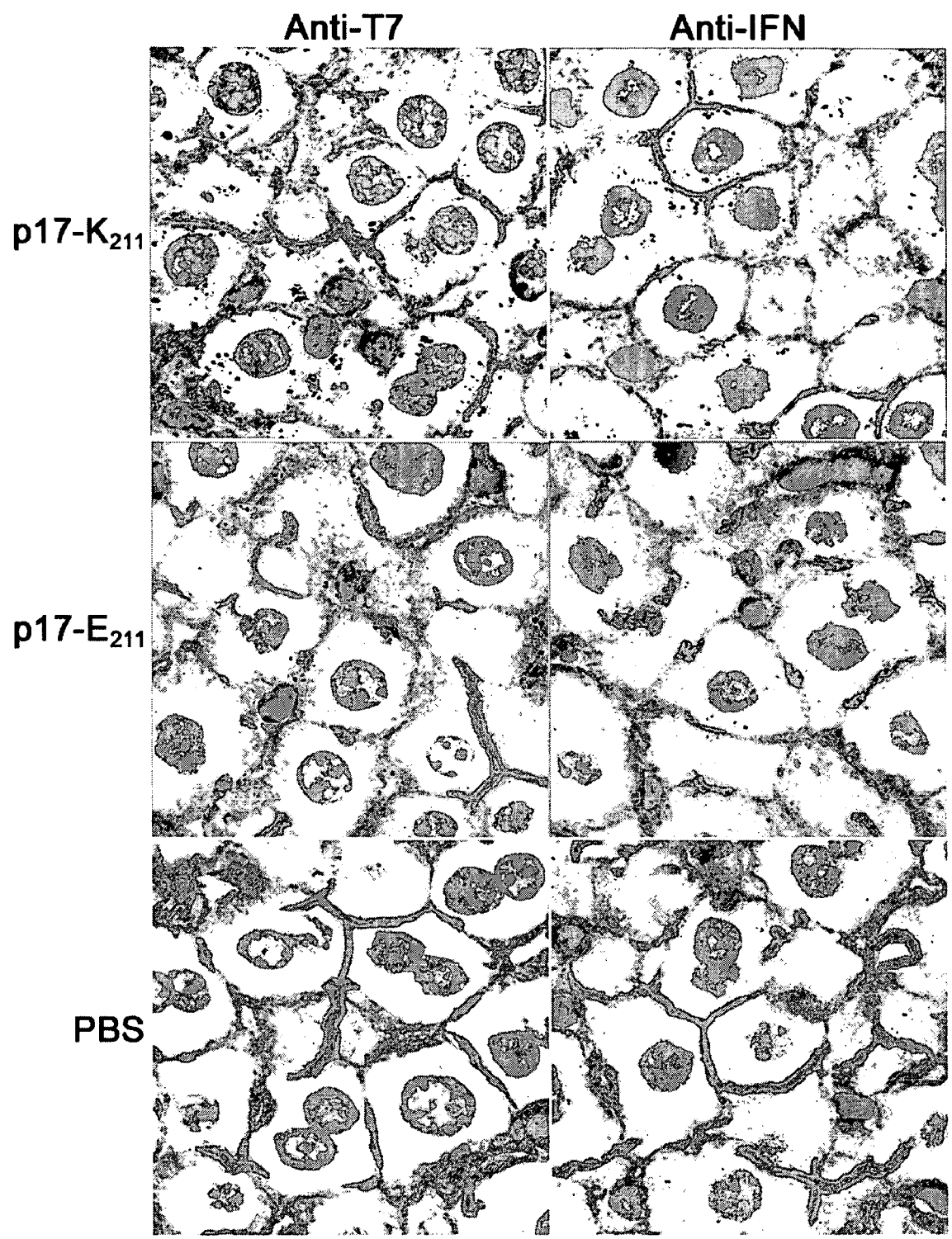
FIG. 6. Targeting of interferon α2b to hepatocytes with p17-$K_{211}$. Interferon-p17-$K_{211}$ or interferon-p17-$E_{211}$ was injected into mice through the tail vein. After 15 min, the livers were removed, sectioned and immunohistochemically stained for either phage protein (anti-T7 phage antibodies) or interferon (anti-IFN antibodies) on separate sections. Livers of the animals injected with PBS served as negative controls (PBS). T7 phage and interferon-p17 are seen in black; nuclei and F-actin in gray.

5. The T7 Ligand targets interferon α2b to hepatocytes in vivo: Hepatocyte targeting was also observed with a more therapeutically relevant fusion protein composed of interferon α2b fused to the p17 rod domain. The full-length human interferon α2b coding region was amplified by PCR by using the pRRB20IF-23 plasmid (ATCC) as a template. NdeI sites were incorporated into both forward and reverse primers, 5'-gctgctctCATATGtgtgatctgcctcaaacccacagcctg gg-3' (SEQ ID 10) and 5'-tgaaccagCATATGttccttacttct-taaactttcttgcaagtttgttgaca-3' (SEQ ID 11), respectively. The amplified fragment was digested with NdeI, gel purified and subcloned into the NdeI digested and dephosphorylated pET28b that encoded the p17 rod domain (residues 150–289) with either $K_{211}$ or $E_{211}$. Recombinant fusion proteins were prepared using the Rosetta® DE3 E.coli cells (Novagen) and purified by using Ni-NTA Agarose (Qiagen) affinity chromatography. Purified recombinant proteins were analyzed by SDS-PAGE and found to be >95% pure. The liver targeting by interferon/p17 fusion proteins was tested by injecting 50 μg of protein in PBS into the mouse tail vein. Livers were removed 15 min after injection and sectioned as above. The fusion protein was detected as describe above using either rabbit anti-T7 antibodies (FIG. 6) or rabbit anti-human interferon antibodies (FIG. 6) on separate tissue sections. All images represented a flattened projection of a stack of twelve 0.4 μm sections. The interferon/ p17-$K_{211}$ fusion protein was detected mostly in hepatocytes (FIG. 6, row 1), while the interferon/ p17-$E_{211}$ fusion protein was occasionally seen in sinusoidal areas (FIG. 6, row 2). This observation further establishes the functional role of the rod domain within p17 for hepatocyte targeting.

6. Targeting of recombinant p17 proteins to monkey hepatocytes. Recombinant full-length p17 proteins were prepared as previously described. Purified p17 proteins, 500 μg of p17-$K_{211}$ or p17-$E_{211}$ in 33 ml of PBS, were slowly injected into monkeys via subcutaneous vein in arm. Liver samples were excised 1 h after injection, submerged in O.C.T. freezing medium and snap frozen in liquid nitrogen. Frozen liver sections (5–7 μm) were prepared using a cryostat and air-dried. Immunofluorescence detection for p17 proteins was performed as described above. Liver sections from an uninjected monkey were used as a control. Images represent an area of 75 μm² from a flattened composite of 8 consecutive confocal optical sections (each 0.4 μm thick). P17 is seen in black, cell nuclei in gray, F-actin in gray near basolateral membranes and in near bile capillary membranes.

Figure 7:
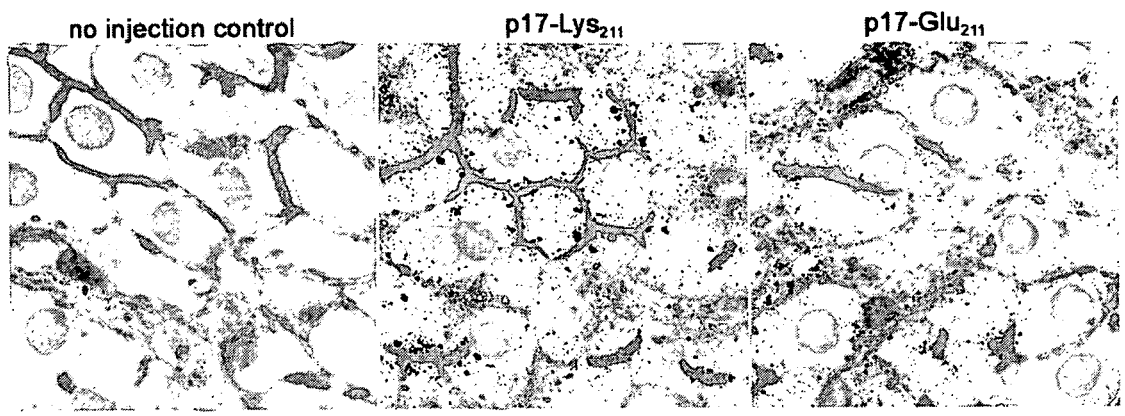
FIG. 7. Targeting of recombinant p17 proteins to monkey hepatocytes. 500 μg p17-$K_{211}$ (p17-$Lys_{211}$) or p17-$E_{211}$ (p17-$Glu_{211}$) was injected into monkey via subcutaneous vein in arm. Liver samples were excised 1 h after injection and frozen liver sections (5–7 μm) were prepared using a cryostat and air-dried. Immunofluorescence detection for p17 proteins was performed as described. Liver sections from monkey receiving no injection were used for immunofluorescence staining control. Images represent an area of 75 μm$^2$ from a flattened composite of 8 consecutive confocal optical sections (each 0.4 μm thick). P17 is seen in black. Cell nuclei and F-actin are gray.

Our data show that p17-$K_{211}$ efficiently targets to monkey hepatocytes (FIG. 7). While some signal was also detected in non-parenchymal cells, control liver sections, from uninjected monkey, showed similar non-parenchymal staining indicated crossreactivity of the anti-T7 antibody. No signal was detected when primary antibody (anti-T7) was omitted from staining procedure (not shown). Hepatocyte targeting deficient p17-$E_{211}$ proteins were primarily localized to non-parenchymal cells. The intensity of the signal in these cells was much stronger than those found in control tissues. Only a small amount of p17-$E_{211}$ was found in hepatocytes.

7. Targeting of exogenous cargo to hepatocytes by recombinant p17 proteins. Hepatocyte targeting of recombinant p17-cytokine, interferon and p17-EYFG fusion proteins indicated the usefulness of p17 as a hepatocyte delivery agent. However, production of fusion protein may not be always advantageous. Therefore, delivery of exogenous cargo by chemical conjugation to p17 provides a more versatile approach.

A. Purified recombinant full-length p17-$K_{211}$ and p17-$E_{221}$ were biotinylated using the amine reactive reagent NHS-LC-LC-biotin (Pierce, Rockford, Ill.) at a 1:1.5 molar ratio in PBS solution containing 0.1M sodium bicarbonate, pH 8.5. P17 conjugates were separated from excess unconjugated reagent using a G50 spin column. Biotinylated p17 (~75 μg) was mixed with Alexa 488 labeled streptavidin (SA) at a p17/SA ratio of 1:1.5 and injected into mice via tail vein as described above. Alexa 488 SA and free biotin were injected in control animals. Animals were sacrificed 15 min after injection and liver sections were frozen and prepared for confocal microscopy.

Figure 8:
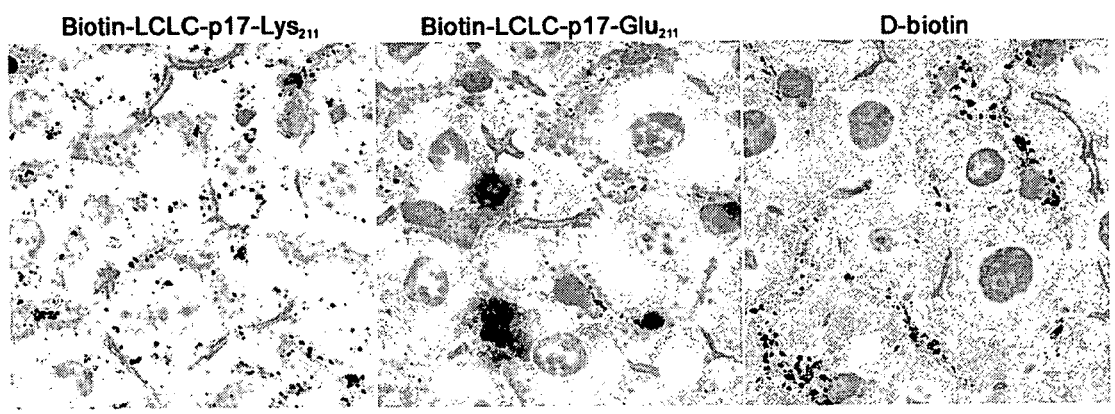
FIG. 8. Targeting of Alexa 488 streptavidin (SA) to mouse hepatocytes by biotinylated full-length p17 proteins. 75 μg biotinylated p17-$K_{211}$ (p17-$Lys_{211}$) or p17-$E_{211}$ (p17-$Glu_{211}$) was mixed with Alexa 488 SA at a p17/SA ratio of 1:1.5 and injected into mice via tail vein. Alexa 488 SA and free biotin conjugate were also injected for background uptake control. Animals were sacrificed 15 min after injection. Frozen liver sections were prepared and counterstained and analyzed as described. Images represent an area of 75 μm$^2$ from a flattened composite of 10 consecutive confocal optical sections (each 0.4 μm thick). Alexa 488 SA is seen in black. Cell nuclei and F-actin are gray.

Liver distribution of Alexa 488 SA signal indicates that only biotinylated p17-$K_{211}$ was able to deliver a significant amount of SA to hepatocytes (FIG. 8), although SA was also found in non-parenchymal cells. In contrast, SA conjugated to free biotin or to biotinylated-p17-$E_{211}$ was found primarily in non-parenchymal cells with minimal signals found in hepatocytes. The SA signal associated with nonparenchymal cells in the p17-$K_{211}$ injected sample may result from inactivation of the p17 targeting determinant due to biotinylation. No effort was made to preserve the targeting determinant during this particular biotinylation procedure. Biotinylation of the lysine at position 211, for instance, would be expected to disable the targeting determinant. Also, free SA was not separated from SA associated with p17 prior to injection in this experiment. Therefore, non-parenchymal localized SA may represent free SA.

B. The p17 rod-domain sequence that is predicted to comprise the targeting determinant does not contain a cysteine residue. Therefore, a cysteine residue was introduced into the rod domain to facilitate cargo conjugation using the cysteine thiol. A cysteine residue was incorporated at the N-terminus of a truncated rod-domain peptide, p17 residues 147–220, by PCR mutagenesis. The primers used were 5'-ggaattcCATATGtgtgatgctgttccgtttggtca-3' (SEQ ID 12) and 5'-cgcGGATCCttagtattgaccagccgtattct-3' (SEQ ID 13) containing the NdeI and BamHI restriction sites, respectively. The resultant PCR fragment was cloned into pET28b (Novagen) using the NdeI and BamHI restriction sites. An 11.5 kDa N-terminal His-tagged Cys recombinant protein containing a rod-domain fragment was produced, Cys-p17Y-$K_{211}$. A construct containing the $E_{211}$ mutation, Cys-p17Y-$E_{211}$, was similarly generated. Purified recombinant Cys-p17Y-$K_{211}$ and Cys-p17Y-$E_{211}$ were biotinylated using the thiol selective PEO-iodoacetyl biotin (Pierce) at 10-fold molar excess in PBS, pH 7.4 following manufacturer's instructions. Biotinylated proteins were purified using a G50 spin column. Alexa 488-labeled streptavidin (SA) from Molecular Probes (Eugene, Oreg.) was added to the biotinylated p17 proteins at a molar ratio of 0.33:1 and injected to mouse tail vein as described above. Animals were sacrificed 15 min after injection, liver samples removed and frozen liver sections for microscopic analysis were prepared as described.

Figure 9:
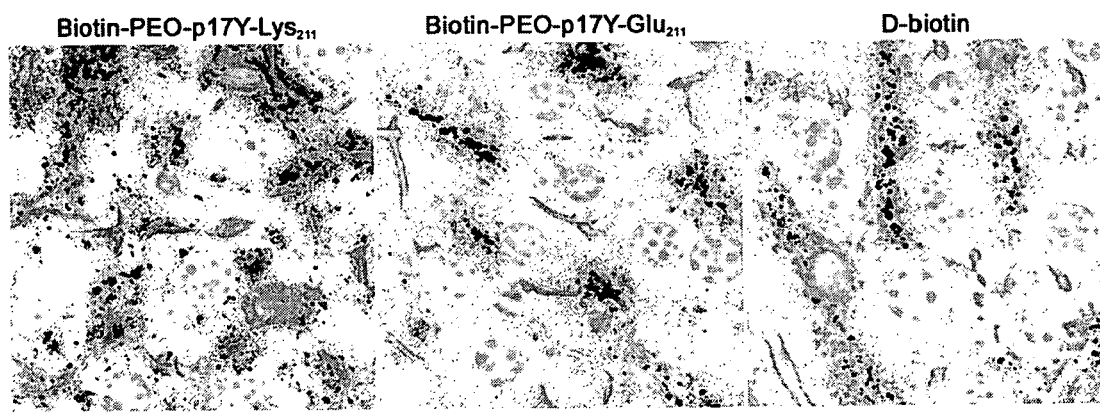
FIG. 9. Targeting of Alexa 488 streptavidin (SA) to mouse hepatocytes by biotinylated p17 rod-domain proteins. Alexa 488 labeled SA was added to the biotinylated p17-$K_{211}$ (p17-$Lys_{211}$) or p17-$E_{211}$ (p17-$Glu_{211}$) rod-domain proteins at a molar ratio of 0.33:1 and injected into mouse via the tail vein. Animals were sacrificed 15 min after injection and liver samples removed and frozen liver sections for microscopic analysis were prepared as described. Images represent an area of 75 μm$^2$ from a flattened composite of 10 consecutive confocal optical sections (each 0.4 μm thick) .Alexa 488 SA is seen in black. Cell nuclei and F-actin are gray.

Biotinylated Cys-p17Y-$K_{211}$ was able to deliver Alexa 488 SA to hepatocytes (FIG. 9). However, most of the SA signal was present in non-parenchymal cells. In contrast, minimal hepatocyte targeting was detected for biotinylated Cys-p17Y-$E_{211}$. The PEO-iodoacetyl biotin may have modified the $K_{211}$ residue. Also, efficiency of biotinylation may have been low. Further optimization of conjugation may improve targeting efficiency. Nevertheless, the Cys-p17Y-$K_{211}$ provides better hepatocyte targeting than the non-specific Cys-p17Y$E_{211}$ peptide.

8. Delivery of exogenous cargo by synthetic p17 peptide to mice and monkey hepatocytes. To further define the location of the targeting signal within the p17 rod domain sequence, synthetic p17 peptides were produced and their ability to deliver exogenous cargo to hepatocytes was assessed. The flexibility in synthesis and design of synthetic p17 peptides or their analogs will facilitate the incorporation of a functional group for conjugation to desired cargo. This approach also alleviates the undesirable effects of random modification of p17 amino acid residues.

A. Delivery of streptavidin (SA) by a biotinylated p17 peptide (MC893). A biotinylated p17 peptide, residues 186–218, was synthesized using a peptide synthesizer (Applied Biosystems) and F-MOC chemistry: Mirus compound number MC893, biotin-$PEG_4$-$PEG_4$-Lys-Asn-Glu-Ser-Ser-Thr-Asn-Ala-Thr-Asn-Thr-Lys-Gln-Trp-Arg-Asp-Glu-Thr-Lys-Gly-Phe-Arg-Asp-Glu-Ala-Lys$_{211}$-Arg-Phe-Lys-Asn-Thr-Ala-Gly (SEQ ID 1). For synthesis, a $dPEG_4$-biotin acid group was incorporated onto a deprotected N-Fmoc-amido-$dPEG_4$-peptide while the peptide was still on the resin. Reagents for peptide synthesis were obtained from Calbiochem and $dPEG_4$-biotin and N-Fmoc-amido-$dPEG_4$ linker from Quanta Biodesign. Similarly, biotinylated p17-$E_{211}$ peptide was also synthesized for targeting specificity control, MC910. Purified peptide was mixed with 250 μg of Cy3-labled SA (Jackson ImmunoResearch Laboratories, Inc. West Grove, Pa.) at peptide to SA molar ratios of 1.2:1, 9:1, 18:1, 45: 1, and 90:1 in a solution containing 25 mM HEPES, 125 mM NaCl, pH 8. The mixtures were injected into mice via the tail vein (400 μl injection volume). For monkey injection, 3.3 mg MC893 peptide was mixed with 3 mg of Cy3-SA, a 13:1 molar ratio, and purified using a G50 column. The sample was recovered in 12 ml 25 mM HEPES, 125 mM NaCl, pH 8 and slowly injected into a Cyno monkey via a subcutaneous vein in the arm. All animals were sacrificed 10 min after injection and liver samples were excised and frozen tissue sections prepared and placed onto microscopic slides. Air dried tissue sections were fixed and counterstained with Alexa 488 phalloidin and To-Pro-3 as previously described and analyzed by confocal microcopy.

Figure 10:
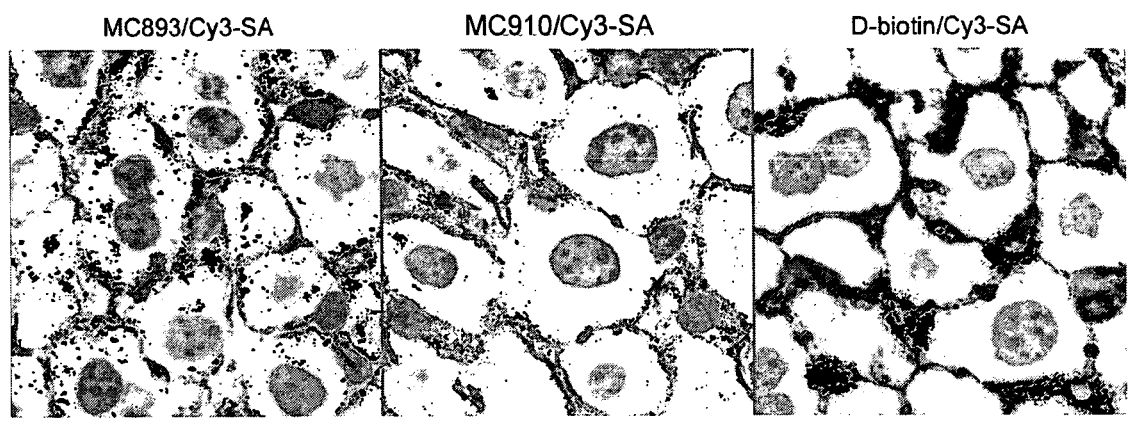
FIG. 10. Delivery of Cy3-labeled streptavidin (SA) by biotinylated synthetic p17 peptide (MC893) to mouse hepatocytes. P17 peptide MC893 and MC910 were mixed with Cy3 labeled SA at a molar ratio of 18:1 and injected into mouse tail vein. Animals were sacrificed 10 min after injection and liver samples removed and frozen liver sections for microscopic analysis were prepared as described. Images represent an area of 75 μm² from a flattened composite of 8 consecutive confocal optical sections (each 0.4 μm thick). Cy3-SA conjugate is seen in black. Cell nuclei and F-actin are gray.
Figure 11:
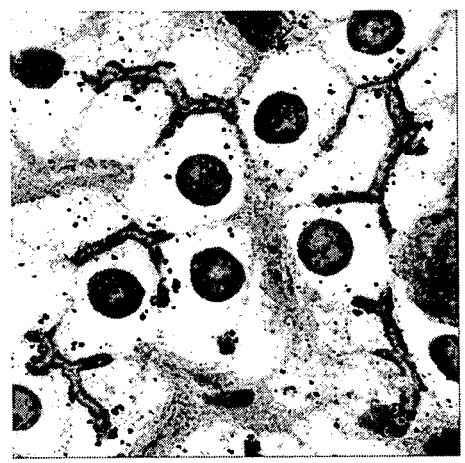
FIG. 11. Delivery of streptavidin (SA) by biotinylated synthetic p17 peptide (MC893) to monkey hepatocytes. P17 peptide MC893 was mixed with Cy3 labeled SA at a molar ratio of 13:1 and injected via subcutaneous vein in the arm. The animal was sacrificed 10 min after injection and liver samples removed and frozen liver sections for microscopic analysis were prepared as described. Image represents an area of 75 μm² from a flattened composite of eight consecutive confocal optical sections (each 0.4 μm thick). Cy3-SA conjugate is seen in black. Cell nuclei and F-actin are gray.

The p17 peptide MC893 efficiently targeted Cy3-SA to hepatocytes in mouse and monkey at peptide to SA molar ratio of 18:1 (FIG. 10 and FIG. 11). MC908, which has the same amino acid sequence as MC893 except for a Lys to Glu mutation at position 211, showed a much lower hepatocyte targeting efficiency. At MC893 to SA ratios higher than 18:1, a dose dependent decrease in targeted signal was observed indicating competition for binding to a saturable site, such as a hepatocyte specific receptor (data not shown). At ratios lower than 9:1, the majority of Cy3-SA signal was on or near basolateral membranes of hepatocytes and sinusoidal cell membranes, suggesting insufficient targeting moiety (data not shown).

B. Delivery of biotinylated cargo by SA-p17 peptide conjugates. An N-terminus Cys peptide corresponding to p17 residues 186–218 was synthesized using a peptide synthesizer (Applied Biosystems) and F-MOC chemistry: Mirus compound number MC892, Cys-$PEG_4$-Lys-Asn-Glu-Ser-Ser-Thr-Asn-Ala-Thr-Asn-Thr-Lys-Gln-Trp-Arg-Asp-Glu-Thr-Lys-Gly-Phe-Arg-Asp-Glu-Ala-Lys$_{211}$-Arg-Phe-Lys-Asn-Thr-Ala-Gly (SEQ ID 1). 2 mg SA was dissolved in 200 μl $dH_2O$ and added to a 200 μl 100 mM sodium phosphate/300 mM NaCl/2 mM EDTA, pH 7.2. A 10 mole equivalent of SPDP (Pierce) dissolved in DMF at 10 mg/ml was then added to the SA solution and mixed at RT for 1 h. The SPDP-modified streptavidin was then purified using a G-25 Sephadex column. It was determined that each SA molecule contained an average of 1.8 PDP groups based on a pyridine-2-thione assay. The SA-PDP conjugate was added to MC892 at a 1:18 molar ratio and incubated for 24 h at 4° C. The MC892-SA conjugates were purified on a G-25 Sephadex column. The sample was then freeze-dried and dissolved in a solution of 25 mM MES, 125 mM NaCl, pH 6.5 at 3 mg/ml.

One mg of NHS-PEG$_4$-Biotin suspended in dry DMF at 10 mg/ml was added to 30 mg amino dextran (Molecular Probes, 70 kDa, 17.9 mole amine per polymer) that was dissolved in 0.1 M NaHCO$_3$ at 10 mg/ml (molar ratio of 4.5 to 1). This solution was mixed overnight at room temperature, transferred into cellulose tubing (Fisher, 12–14,000 MWCO) and dialyzed once against 20 L 20 mM NH$_4$Cl followed twice against 5 L dH$_2$0. The dialyzed sample was lyophilized. The sample was then dissolved in dH2O at 30 mg/ml. Each dextran polymer was estimated to contain an average of 0.5 biotin group. This biotinylated dextran was fluorescently labeled with Cy3-OSu (Amersham) at a weight ratio of 1:0.074. Excess free dye was removed using a Sephadex G-50 column. Labeled dextran was eluted in 25 mM NH$_4$CO$_3$. The sample was freeze dried and resuspended at 7.5 mg/ml in 25 mM HEPES/125 mM NaCl, pH 8.0. Biotinylated siRNA (5'-biotin-LC-siRNA, Dharmacon) was labeled with Cy3 using Cy3 LabelIT (Mirus Corp) according to manufacturer's instructions.

Delivery of biotinylated Cy3-labeled 70 kDa dextran and siRNA to mouse hepatocytes: Biotinylated Cy3-dextran (32.5 μg) was mixed with MC892-SA (25 μg) at a biotin/SA molar ratio of 1:1. The same amount of biotinylated Cy3-dextran without MC892-SA was injected as a control. For siRNA delivery, MC892-SA (23 μg) or Alexa 488-SA (23 μg) was mixed with biotinylated Cy3-siRNA (30 μg) and applied to a G-25 spin column equilibrated with 25 mM HEPES, 125 mM NaCl, pH 8.0. Samples were injected into mice via the tail vein.

Liver samples were removed 10 min after injection, placed into OCT freezing medium and snap frozen in liquid nitrogen. Frozen liver sections (5–7 μm thick) were prepared and counterstained with Alexa 488 phalloidin for F-actin and To-Pro-3 for cell nuclei. Processed slides were mounted in Vectorshield (Vector Laboratories, Burlingame, Calif.) and analyzed using a Zeiss LSM510 confocal microscope.

Figure 12:
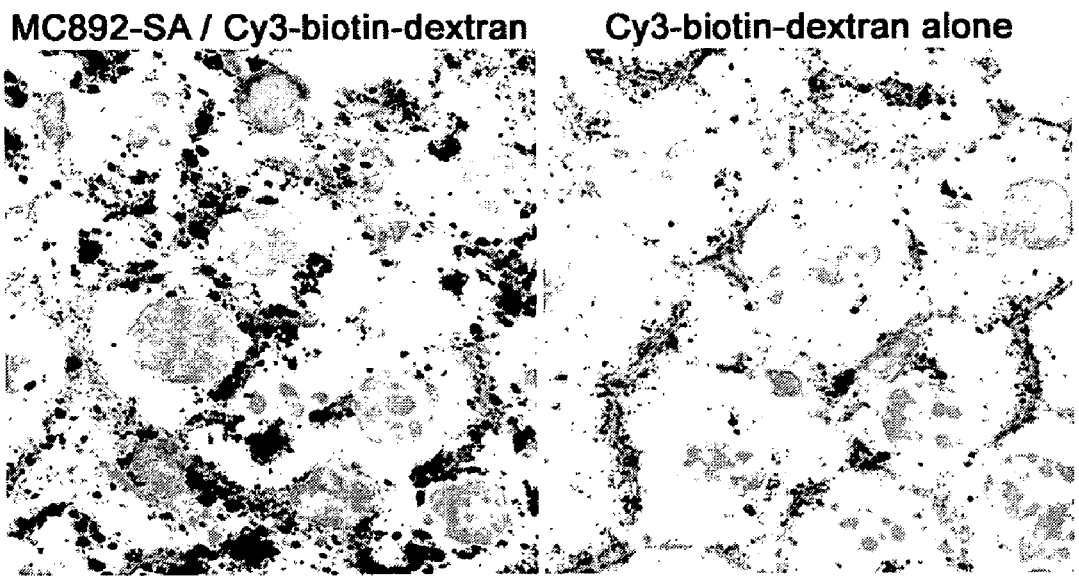
FIG. 12. Delivery of biotinylated Cy3-labeled 70 kDa dextran to mouse hepatocytes by MC892-SA conjugate. Biotinylated Cy3-labeled 70 kDa dextran (32.5 μg) was mixed with MC892-SA (25 μg) conjugate at a biotin/SA molar ratio of 1:1 and injected into mouse tail vein. The same amount of biotinylated Cy3-labeled dextran without MC892-SA added was injected to determine the level of non-specific delivery. Animals were sacrificed 10 min after injection and liver samples removed and frozen liver sections for microscopic analysis were prepared as described. Images represent an area of 75 μm² from a flattened composite of 8 consecutive confocal optical sections (each 0.4 μm thick).Cy3-dextran is seen in black. Cell nuclei and F-actin are gray.
Figure 13:
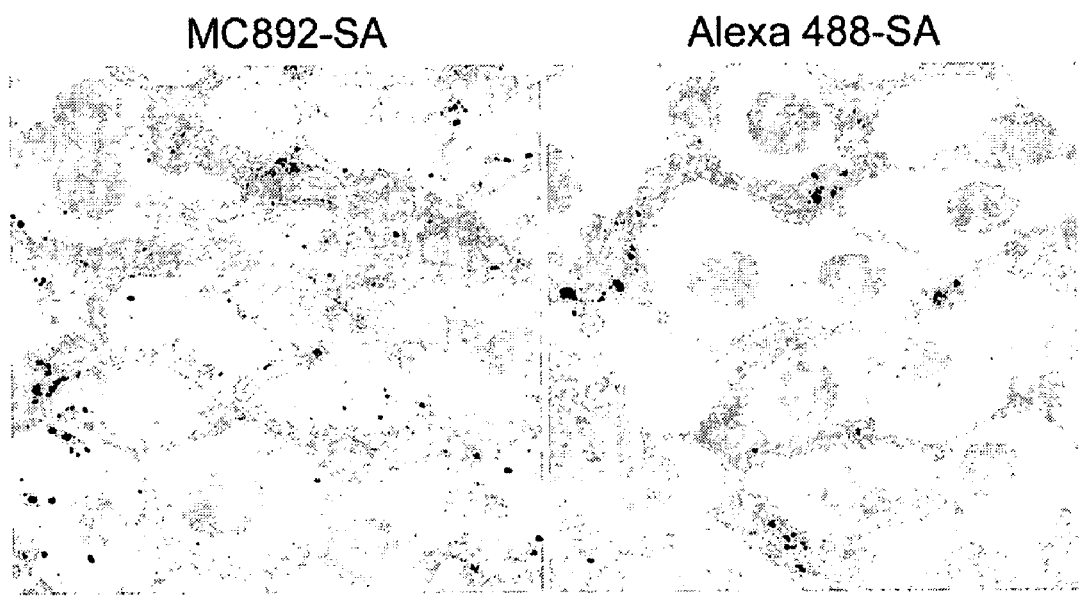
FIG. 13. Delivery of biotinylated siRNA to mouse hepatocytes by MC892-SA conjugate. MC892-SA (23 μg) or Alexa 488-SA (23 μg) was mixed with Cy-3 labeled biotinylated siRNA (30 μg) and applied to a G-25 spin column equilibrated with 25 mM HEPES, 125 mM NaCl, pH 8.0. Samples were then injected into mice via the tail vein. Images represent an area of 75 μm² from a flattened composite of 10 consecutive confocal optical sections (each 0.4 μm thick). Cy3-siRNA is seen in black. Cell nuclei and F-actin are gray.

At 10 min after injection, high levels of Cy3-dextran signal was observed inside hepatocytes, with additional signal near the basolateral membrane of hepatocytes (FIG. 12). At 20 min (not shown), signal near basolateral membrane was substantially decreased with internalized Cy3-dextran signals found in clusters near cell nuclei. The low level of non-targeted uptake of biotinylated Cy3-dextran that was detected may be eliminated by blocking the remaining dextran amino groups. Direct attachment of the T7 ligand to dextran via a covalent linkage also resulted in targeting of the dextran to hepatocytes (data no shown). Cy3-siRNA signal was detected in mouse hepatocytes injected with targeting peptide whereas no hepatocyte Cy3-siRNA signal was detected in the control animal (FIG. 13), indicating successful targeting of siRNA to the liver by MC892.

9. Targeting of nucleic acid complexes to liver using a T7 ligand: DNA/PLL/biotinylated-SPLL complexes (1:3:10 molar ratio) were formed in 25 mM HEPES by first combining the DNA and PLL followed by addition of SPLL. The DNA was plasmid DNA encoding a human factor IX expression cassette. PLL is poly-L-lysine of molecular weight 20–35 kDa. SPLL is succinylated PLL. The particles were then crosslinked by the formation of covalent bonds between carboxyls on SPLL with amines and PLL. SA-MC892 was then added to the DNA/PLL/biotinylated SPLL crosslinked particles at a biotin to MC892 molar ratio of 1:2. The resultant particles, containing both DNA and liver targeting ligands, can then be injected into mice via tail vein as described.

10. Targeting of liposomes to the liver using a T7 ligand: Egg PC, DOPE-Cy3, DOPE, cholesterol liposomes were made at the weight ratio 62.5:10:2.5:25. DOPE was either unmodified, DOPE-PDP, or DOPE-PDP-MC892. Alternatively, DOPE-biotin combined with streptavidin-PDP-MC920 was used. MC920 is identical to MC892, except for having a longer PEG spacer. Lipids were combined with or without nucleoside analogs in chloroform and dried in a rotary evaporator overnight. The dried lipids were then reconstituted in isotonic saline solution, sonicated and extruded to form 100 nm liposomes. For liposomes made with DOPE-PDP, MC892 was added at a 3 mole excess of MC892 to PDP groups and allowed to react overnight at 4° C. Liposomes are then injected into the tail vein of mice. At various time, the livers are harvested and localization of the liposomes determined by fluorescence microscopy. Increased amounts of liposomes were observed in hepatocytes when the liposomes were formulated using T7 ligand peptide conjugated DOPE (data not shown).

11. Determination of particle size on the efficiency of targeting to hepatocytes: T7 ligands are bound to: fluorescent-streptavidin/gold (SA-gold) particles 2, 5, 10, 15, 20, 30, 40, 50, 60, 80, 100, 150, 200 and 250 nm in diameter; neutral, positively charged, or negatively charged microspheres (Polysciences) 50 nm and 200 nm in diameter; or liposomes 30–300 nm in diameter. Liposomes are labeled with an internal aqueous (fluorescein-dextran) or with membrane-bound fluorescent probe (e.g., N—Rh—PE (N-(lissamine rhodamine B sulfonyl) phosphatidylethanolamine. For attachment to SA-gold particles, T7 ligand-biotin conjugates are used. For attachment to microspheres and liposomes, thiol containing T7 ligands such as cysteine-containing peptides are used. For some experiments, the particles are labeled with $^{125}$I. The amount of peptide or protein attached to the particles is varied to determine the number or density of hepatocyte-targeting ligands required for targeting.

At 5, 15, 30, 60, and 180 min after injection of the gold particles into the tail vein of mice (≦400 μl injection volume), the mice are sacrificed and the livers and other organs excised. For microscopy analyses, the organs are placed into OCT (Fisher) freezing medium, snap frozen in liquid nitrogen, cryo-sectioned, and placed onto slides The slides are then processed for confocal fluorescent microscopy and electron microscopy. Various cell types are determined by morphology and by immunohistochemical detection of cell-type specific markers. Targeting efficiency is quantitated by counting the particles in a select number of cells or with $^{125}$I radioactivity. For radioactive analyses, liver cells are sorted to determine the quantitative distribution among parenchymal and non-parenchymal cells.

12. Identification of the T7 ligand receptor: The identification and cloning of the putative T7 ligand receptor will provide an important tool for elucidation of the pathway through which hepatocytes internalize structures containing the T7 ligand as well as for the development of additional T7 ligands for therapeutic delivery to the liver. For example, a synthetic chemical analogue of erythropoietin was developed by screening a combinatorial chemical library of dimeric iminodiacetic acid diamides for binding to the erythropoietin receptor [Goldberg J et al. 2002]. Identification and purification of the receptor is accomplished using affinity techniques. Cells expressing the receptor, such as cultured hepatoma cells or isolated hepatocytes, are incubated at 4° C. with an affinity ligand: T7 phage, p17, or other compound containing a known T7 ligand. Cells demonstrating selective binding of known functional T7 ligands, but not inactive $E_{211}$ variants will be used as a source of the T7 ligand receptor. Hepatocytes that are maintained for a few days in a Matrigel culture in order to restore the expression of hepatocyte surface antigens may be employed. The affinity ligand may be conjugated to biotin or a cleavable radioiodinated photoreactive cross-linker (N-[4-(p-azidosalicylamido)butyl]-3'-(2'-pyridyldithio)propionamide) or both. Cross-linking provides more stable interaction between the ligand and the receptor during the purification process. After binding of the affinity ligand to cells, unbound ligand is washed away with cold TBS/1 mM $CaCl_2$/1 mM $MgCl_2$. The sample is then irradiated at 302 nm to activate the azide group of the crosslinker, if present, resulting in cross-linking of the ligand to the receptor.

Washed cells are lysed at 4° C. by a non-ionic detergent or by a mixture of non-ionic and ionic detergents, such as Triton X100 and sodium deoxycholate, in TBS/1 mM $CaCl_2$/1 mM $MgCl_2$ containing protease inhibitors. The presence of $Mg^{2+}$ is required to prevent nuclear lysis. The solubilized receptor-ligand complex is removed from the cell lysate by an immobilized agent, such as antibody or streptavidin. Proteins can be separated from cross-linked ligand by addition of 10 mM DTT or 100 mM β-mercaptoethanol. Proteins bound to the T7 ligand are analyzed by one- and two-dimensional gel electrophoresis. Control samples using inactive $E_{211}$ T7 ligand variants are used for comparison. Proteins specifically bound to the T7 ligand are then recovered and microsequenced. The amino acid sequence information is used to search gene/protein databases or to design primers for PCR amplification of genomic DNA or reverse transcribed mRNA. If the receptor is non-proteinaceous, then a photo-cross-linking approach to look for other types of molecules, such as saccharides, is employed.

RT-PCR, Northern blot analysis, immunoblot and immunohistochemistry analyses are possible once the receptor has been identified. These analyses are used to determine expression levels of the receptor in various cell types. It is possible that the T7 ligand receptor is present on other cell types is only accessible to the receptor on hepatocytes because of the sinusoid fenestrae present in the liver. Conformation of the role of the identified receptor in binding and internalizing the T7 ligand is accomplished by expressing the recombinant receptor in cell types that do not normally express the receptor. If expression of receptor cDNA in receptor negative cells lines—those that do not bind the T7 ligand—confers on these cell the ability to bind and internalize T7 ligands and T7 ligand conjugates, then the cloned receptor is sufficient. SiRNA technology is used in receptor positive cells to inhibit expression of the endogenous receptor. If inhibition of receptor expression in these cells knocks out T7 ligand binding, then the cloned receptor is necessary for T7 ligand binding and internalization.

13. Determination of Hepatocyte Targeting Peptide Consensus Sequence: The identification of the residues that are required for hepatocyte targeting should aid in the design of synthetic peptides and eventually for the design of synthetic chemical mimics. T7 phage is employed to discover a consensus hepatocyte targeting peptide sequence. A T7 phage library displaying random amino acid residues within the predicted hepatocyte-targeting region (amino acids 171–231 of protein p17) is constructed. Random mutations are made within this sequence such that the theoretical complexity of the library corresponds to ≦6 amino acid changes per phage clone. To select for sequences that retain T7 ligand function, hepatocyte targeted phage are isolated 1–60 min after mouse tail vein injection of $1\times10^{10}$–$1\times10^{11}$ pfu. Hepatocyte-associated phage are amplified by dissolving hepatocytes in 1 M NaCl/2% Triton X100 and adding the lysate to a culture of E. coli BL21. Amplified phage are isolated by CsCl gradient centrifugation, titered and used for the next selection round. After 3–5 rounds, phage clones that target liver are sequenced. In addition to determining the consensus sequence for phage targeting to liver, selected phage clones will be compared in their kinetics of liver association. Faster kinetics indicates more efficient targeting and possibly higher affinity. Selected hepatocyte targeting sequences are aligned and the importance of each tested position for hepatocyte targeting is evaluated by comparing the diversity of amino acid residues at each position. Residues identified by this screen as important in T7 ligand function will involve amino acids that directly and indirectly contribute to hepatocyte targeting. Directly contributing amino acids are those that are engaged in a physical interaction with the hepatocytes. Indirectly contributing amino acids are those that affect the three-dimensional structure of the ligand or affect phage infectivity and amplification in bacteria. Amino acid substitutions that disrupt infection or amplification in bacterial cells will be underrepresented in the selected library.

A Method of Using T7Phage Library to Determine Consensus Targeting Peptide Sequence.

Based on the knowledge that the T7 peptide derived from amino acids residues 186–218 retained hepatocyte targeting activities, overlapping oligos (with 5' biotins) were designed with random bases incorporated into positions corresponding to amino acids 194, 197, 198, 204, 205, 208, and 211 of the tail fiber protein. Unique BspEI and SacII sites were introduced into gene 17 at positions 511 and 686, respectively, of the gp17 ORF to facilitate the cloning of degenerate oligos.

The vector was digested with BspEI and SacII, and then CIP treated. The oligos were annealed, filled and digested with BspEI and SacII. Insert was mixed with streptavidin, and purified on a 2% agarose gel. Vector and insert were then ligated overnight, packaged, and used to infect 500 ml of BL21 bacteria. The phage library was purified using PEG precipitation, followed by CsCl gradient centrifugation, dialysis and titering. The selections were done with $4\times10^{10}$ pfu per animal. After 4 rounds of selection, plaques were picked and sequenced.

Figure 14:
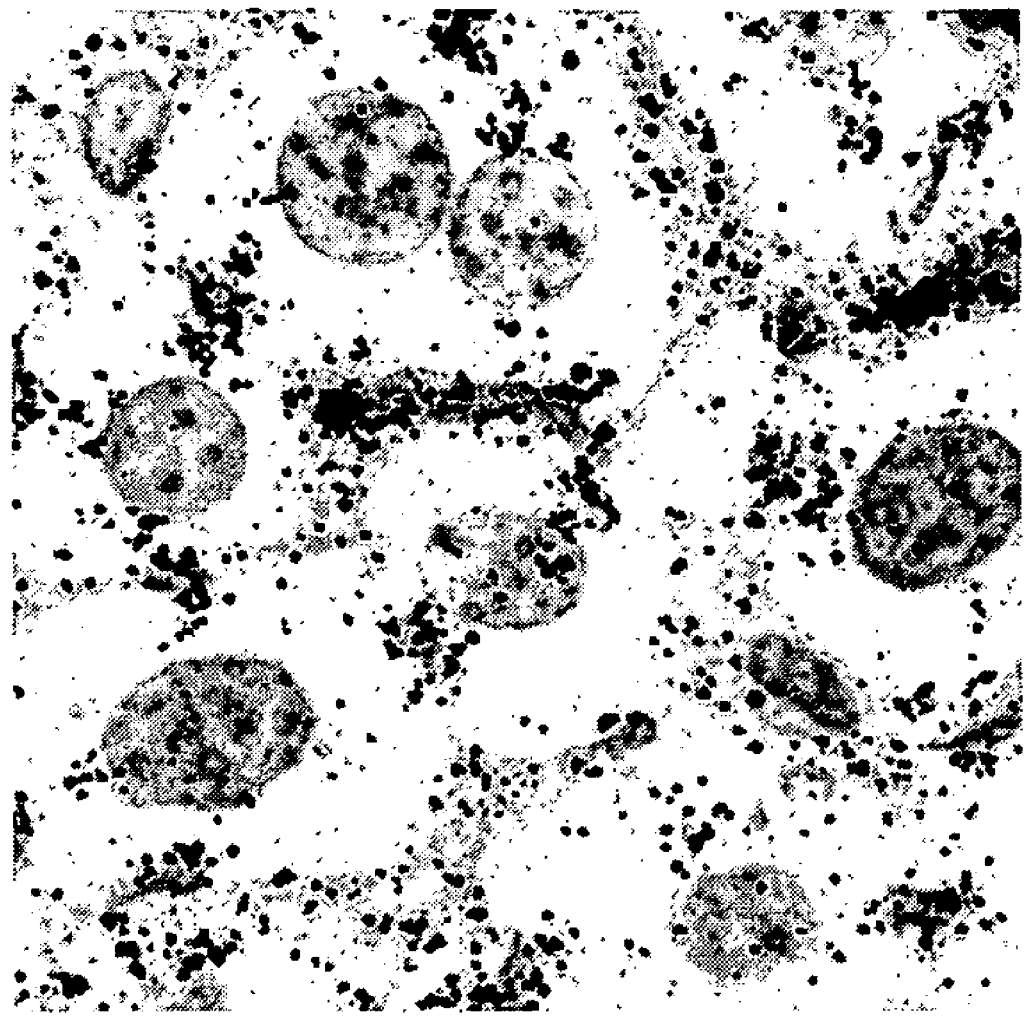
FIG. 14. Targeting of T7 phage to mouse hepatocytes. Purified phage particles (1×10¹¹ pfu) suspended in 250 μl of PBS was injected via the tail vein under low pressure. Liver samples were excised 30 min after injection and frozen liver sections (5–7 μm) were prepared using a cryostat and air-dried. Immunofluorescence detection for T7 phage was performed as described. Images represent an area of 75 μm² from a flattened composite of 10 consecutive confocal optical sections (each 0.4 μm thick). T7 is seen in black, cell nuclei and F-actin in gray.

Phage clones with non-wild type p17 sequence and enriched in liver were analyzed for cell type distribution in liver by immunohistochemistry. A phage clone from this experiment, designated clone#10a was found to retain hepatocyte-targeting activities (FIG. 14). The new targeting p17 sequence contained the following changes from the native wild-type sequence: $K_{197}$ to R, $Q_{198}$ to R, $K_{204}$ to Q, $G_{205}$ to T, $D_{208}$ to I.

14. Identification of high affinity T7 ligands: Competition experiments are used to verify that identified hepatocyte-targeting ligands bind to the same receptor and to determine which identified T7 ligands have the highest affinity for hepatocyte binding. An excess of UV-inactivated T7 phage, T7 ligand or T7 ligand-conjugate is used to compete for hepatocyte binding with another potential T7 ligand. Competition between different T7 ligands is used to determine that affinity of proposed T7 ligands. The competition between live and UV-inactivated phage is determined by measuring live phage uptake by liver as described [Sokoloff AV et al. 2000; Sokoloff AV et al. 2001]. Other competition experiments with other T7-ligand conjugates are also possible. Detection of conjugates can be done by fluorescence microscopy or radioactive measurements. For instance, an EYFP-T7 ligand peptide fusion protein expressed in bacteria and purified using a His tag can be used. Competition experiments can also be carried out using hepatocyte culture cells or purified receptor. Such competition experiments are also used to screen combinatorial chemical and parallel synthesis libraries for non-peptide T7 ligands, screening for displacement of a known pre-bound T7 ligand.

15. Structural requirements for the peptide hepatocyte targeting determinant:

A. P17 mutational analysis—To ascertain whether the coiled coil configuration present in the native p17 protein is important for T7 ligand function, hydrophobic residues present at predicted positions a and d (Table 2) are substituted with hydrophilic residues that promote the formation of α helices but do not form interhelical bonds required for maintaining a coiled coil structure. The loss of hepatocyte targeting by peptide T7 ligands containing such substitutions would serve as an indication that a coiled coil-like structure is an important component of the T7 ligand.

B. Trypsin digestion analysis of phage infectivity—The conformation of the T7 ligand region of T7 phage is further analyzed by trypsin digestion. Trypsin treatment has no effect on the bacterial infectivity of $T7$-$K_{211}$ phage. Phage clones from Example 14 ($10^{10}$–$10^{11}$ pfu/ml) that retain hepatocyte targeting are incubated with 1–100 μg/ml trypsin± inhibitors in TBS/5 mM $CaCl_2$ (pH 8.0) at 37° C. for 30–60 min, diluted, and plated on E. coli BL21 cells. The appearance of trypsin sensitivity in mutant T7 phage indicates that the mutation(s) disturb the coiled coil structure of p17 without affecting liver targeting. The positions of the trypsin-sensitive sites are determined by SDS-PAGE analyses and peptide sequencing of the hydrolysis products.

C. Transmission electron microscopy analyses—The structures of the mutant T7 phage proximal fibers are also analyzed by transmission electron microscopy. The phage tail complexes are dislodged from phage at 50° C. in the presence of EDTA (2 mM, pH 8.0) and isolated by CsCl gradient centrifugation as described [Steven AC et al. 1988]. A straight configuration of the proximal tail fiber—instead of kinks, bulges or bends—indicates that the rod domain does not have any structural irregularities.

D. Detailed analysis of a peptide T7 ligand—We have shown that the synthetic peptide Lys-Asn-Glu-Ser-Ser-Thr-Asn-Ala-Thr-Asn-Thr-Lys-Gln-Trp-Arg-Asp-Glu-Thr-Lys-Gly-Phe-Arg-Asp-Glu-Ala-Lys-Arg-Phe-Lys-Asn-Thr-Ala-Gly (SEQ ID 1) functions as a T7 ligand. In order to define the minimal peptide length required for targeting, sequential truncations of single amino acids are made from both the amino-terminal and carboxy-terminal ends of the peptide. The ability of biotin-peptide conjugates to target Cy3-labeled streptavidin to hepatocytes in mice is determined by confocal fluorescent microscopy as described above. Potential peptide secondary and tertiary structure is examined by CD spectra analyses, chromatography and analytical equilibrium centrifugation. The minimal peptide ligand is also tested in competition experiments with other known T7 ligands. Once the minimum length peptide that retains targeting function is defined, a series of amino acid substitutions are performed to identify which residues are required for interaction with hepatocytes. These substitutions include: alanine scan, D-amino acid scan, all D-amino acid peptide, conservative and non-conservative substitution, and amino acid analog substitution. The targeting efficiency of the resultant peptides is evaluated by confocal fluorescent microscopy and by competition binding. The effect of the substitutions on peptide structure is assessed by CD spectroscopy, size-exclusion chromatography and analytical equilibrium centrifugation.

Amino acids identified as important for targeting are further substituted with amino acid analogs that have predetermined conformational and torsional angle biases. The sequence and structural information obtained from these analyses will aid the development of chemical mimics of the peptide T7 ligands.

16. Display and targeting of constrained T7 ligand peptides:

A. Expression of the hepatocyte targeting determinant on a T7 phage coat protein—Selected T7 ligand peptides are cloned into p10 of the phage vector T7Select-415b and grown in appropriate E. coli cells. Phage grown in E. coli BL21 cells contain display peptides in all copies of the coat protein 10B (415 copies per phage particle) while phage grown in E. coli 5615 cells contain display peptides only in about 20% of coat protein molecules. Peptides are displayed as either linear peptides or constrained peptides. The structure of linear displayed peptides is $NSDGA(X)_n$, where $(X)_n$ is the chosen T7 ligand sequence. The structure of constrained displayed peptides is $NSDGAC(X)_nC$. The constraint imposed on displayed peptides, by disulfide bonds between the cysteine residues, promotes the formation of secondary structure. Because the ligand is expressed on T7 phage, the T7 ligand sequence can be optimized by generating a T7 phage library and selecting clones with the highest hepatocyte binding affinity. Additionally, hydrophobic residues at locations corresponding position a and d of the p17 predicted coiled coil structure are substituted with hydrophilic amino acids as described above. The phage are tested for liver targeting by a plating assay and by immunohistochemistry.

B. Expression of the hepatocyte targeting determinants within the B domain of protein A—The B domain of protein A is 58 amino acids long and contains an α helical bundle composed of three α helices containing 11, 12 and 14 amino acids. The bundle is stabilized by interactions between internal residues of the α helices. However, virtually all external amino acid residues can be mutated without perturbing the overall structure of the bundle [Nord K et al. 1995; Nord K et al. 1995]. Two overlapping oligonucleotides, covering the whole coding region of B domain (174 nucleotides) are amplified by PCR and cloned into a bacterial EYFP expression vector to generate a fusion protein. The oligonucleotide primers contain T7 ligand peptide sequence. For some constructs, only external helix 1 or helix 2 residues of the B domain are substituted for p17 targeting determinant amino acids that correspond to predicted external residues of the coiled coil motif. For these constructs, the B domain tertiary structure is expected to remain intact. For other constructs, the entire B domain helix 1 or helix 2 is substituted for the T7 ligand peptide sequence. For these constructs, the B domain tertiary structure is expected to be disrupted. Changes in the α helicity of the bundles are easily detected by CD spectroscopy. This approach will demonstrate whether the hepatocyte targeting determinant retains its targeting ability when displayed within a heterotrimeric α helical bundle.

C. Expression of selected hepatocyte targeting sequences in a human type III fibronectin domain—The human fibronectin type III domain (FN3) is a small 94 amino acid immunoglobulin-like domain. Sequences coding hepatocyte targeting determinants are cloned into the FN3 gene by replacing the FG loop sequence. Assembly of a synthetic FN3 gene has been previously described in detail by others [Koide A et al. 1998]. T7-ligand-FN3 is then expressed as a fusion with EYFP. The chimeric proteins are tested for liver targeting by confocal microscopy. Because FN3 can be expressed on T7 phage, the T7 ligand sequence can be optimized by generating a T7 phage library and selecting clones with the highest hepatocyte binding affinity.

D. Expression of the hepatocyte targeting sequence within a coiled coil scaffold—The incorporation of a peptide sequence within a coiled coil scaffold should allow the expression of a minimal length amino acid sequence and maintain coiled coil structure. To make a relatively small hepatocyte targeting construct with a coiled coil structure the targeting domain is incorporated into to a known structured triple-stranded coiled coil region of the human mannose-binding protein. Chimeric proteins with EYFP are made and tested for liver targeting using confocal fluorescent microscopy as above. Such hepatocyte targeting constructs can be both fused to therapeutic proteins and attached to particles.

Figure 15:
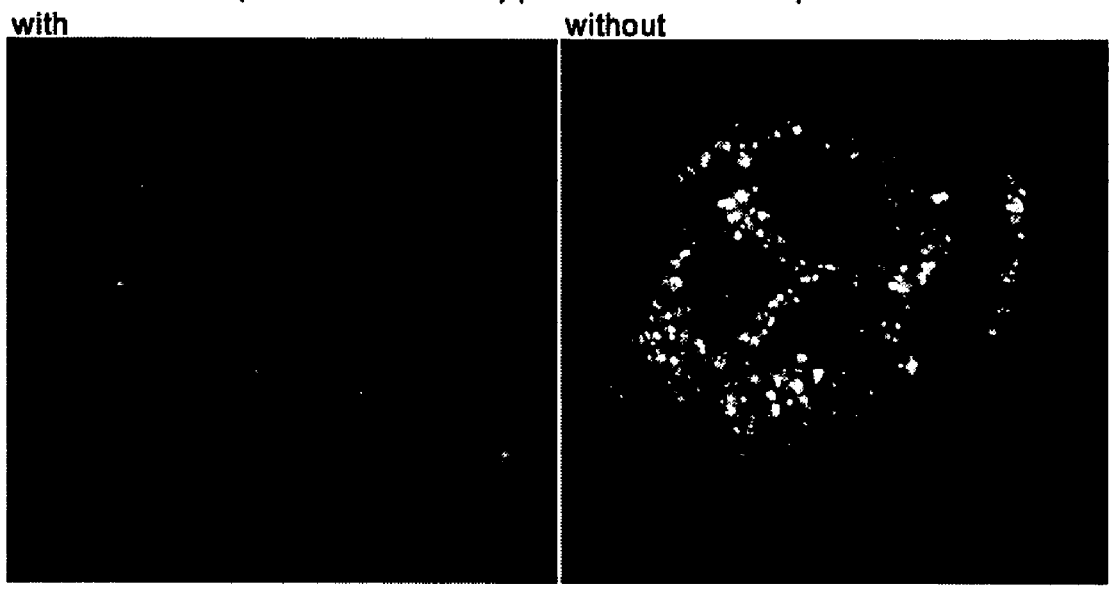
FIG. 15. In vitro T7 ligand functional assay; binding/endocytosis of MC912 T7 ligand conjugated to biotin in cultured mouse hepatoma cells in the presence or absence of excess MC892 T7 ligand. Binding and endocytosis was monitored by co-internalization of Cy3-streptavidin.

17. In vitro T7 ligand functional assay; binding/endocytosis of T7 ligand in cultured mouse hepatoma cells. Mouse hepatoma Hepa1clc-7 cells (ATCC) were maintained in Dulbecco's Modified Eagle's Medium (DMEM, Mediatech, Inc. Herndon, Va.), supplemented with 10% fetal bovine serum+100 mg/ml penicillin and streptomycin at 37° C. in a humidified atmosphere containing 5% $CO_2$. For binding and endocytosis experiments, 150,000 cells in 2 ml media per well were seeded into 6 well culture plates containing a glass cover slip and grown for 24 h. Medium was then removed and replaced with 1 ml pre-warmed Opti-MEM (Gibco-Invitrogen). For each well, 20 μl T7 peptide (MC912)/SA complex (5.5 μg of MC912/5 μg of Cy3-SA, a 13:1 molar ratio) in PBS was added and incubated for 15 min at 37° C. MC912 has the same amino acid sequence as MC892 and is covalently conjugated to biotin. For wells that received excess free peptide, one mg (200-fold) MC892 was added to cells 5 min prior to the addition of T7 peptide/SA complex. Incubation medium was then removed, cells were washed 3× with PBS (3 min each), fixed with 4% formalin in PBS, rinsed in PBS and counterstained with Alexa 488-phalloidin for 20 min. Cells were then rinsed 3× in PBS. Cover slips were removed from the wells and mounted onto glass slides with Vectorshield mounting medium and binding/endocytosis of T7 peptide/SA complexes were evaluated by confocal microscopy T7 peptide (MC912)/Cy3-SA complexes were taken up by Hepa1clc-7 cells efficiently. In the presence of 200-fold excess competing T7 peptide, the binding and uptake of fluorescently labeled T7 peptide/Cy3-SA complexes were essentially abolished, indicating that a receptor mediated uptake mechanism is involved. Cy3-SA without T7 peptide was not taken up by Hepa1clc-7 cells (FIG. 15).

Figure 16:
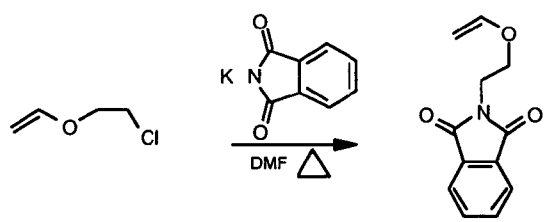
FIGS. 16A–16C. Preparation of alkyl enol ether cationic polymers. (A) Synthesis of 2-vinyloxy ethyl phthalimide monomers. (B) Synthesis of alkyl enol ether cationic polymers. (C) Fluorescent labeling of alkyl enol ether cationic polymers.
Figure 16:
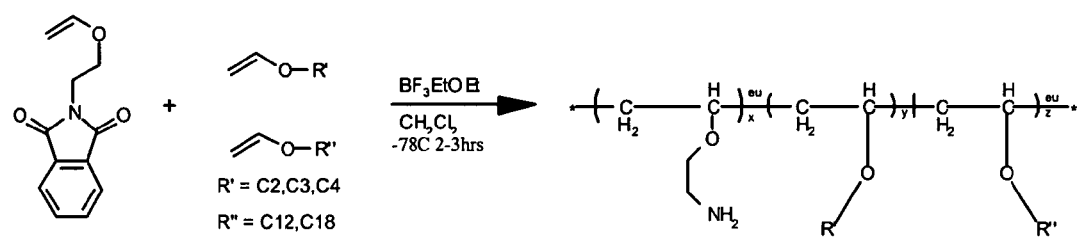
Figure 16:
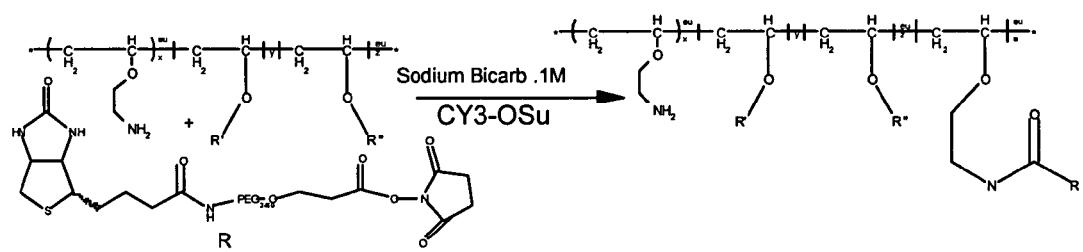

18. Targeting of a polymer to hepatocytes by attachment of multiple T7 ligands to a pH-labile anionic polymer. Preparation of the cationic polymer: 2-Vinyloxy Ethyl Phthalimide (FIG. 16A) as prepared by reacting 2-chloroethyl vinyl ether (25 g, 0.24 mol) and potassium phthalimide (25 g, 0.135 mol) in 75 mL DMF at 100° C. using tetra n-butyl ammonium bromide (0.5 g) as the phase transfer catalyst. This solution was heated for 6 h and then crashed out in water and filtered. The solid was then recrystallized twice from methanol to give white crystals. Varying mole percentages of 2-Vinyloxy Ethyl Phthalimide was added to an oven dried round bottom flask under a blanket of nitrogen in anhydrous dichloromethane. To this solution varying mole percentages of ethyl (C2), propyl (C3), butyl (C4), triethylenegycol (Peg3), and/or butylethylenegycol(EG-C4) enolether were added followed by varying mole percentages of dodecyl (C12) and/or octadecyl (C18) enolether (Table 4). This solution was then brought to −78° C. in a dry ice acetone bath. To this solution 10 mol % $BF_3EtOEt$ was added and the reaction was allowed to proceed for 2–3 h at −78° C. (FIG. 16B). The reaction was then quenched with a methanol ammonium hydroxide solution and brought to dryness under reduced pressure. The dried crude polymer was then brought up in 30 mL of 1,4-dioxane/methonal (2/1) to which 20 mol eq. of hydrazine per phthalimide was added. The solution was refluxed for 3 h and brought to dryness under reduced pressure. The solid was then brought up in 20 mL 0.5M HCl, refluxed for 15 minutes and diluted with 20 mL distilled water and refluxed for additional hour. This solution was then neutralized with NaOH cooled to RT and transferred to 3,500 MWCO cellulose tubing and dialyzed (2×20 L) over 48 h against distilled water and freeze dried.

TABLE 4

Alkyl enol ether cationic polymers

| polymer number | 2-Vinyloxyethyl Phthalimide | C2 | C3 | C4 | EG-C4 | Peg3-Me | C12 | C18 |
|---|---|---|---|---|---|---|---|---|
| MC966 | 87.5% | 7.5% | — | — | — | — | 5% | — |
| MC967 | 75% | 20% | — | — | — | — | 5% | — |
| MC968 | 50% | 45% | — | — | — | — | 5% | — |
| MC969 | 87.5% | — | — | — | 7.5% | — | 5% | — |
| MC970 | 75% | — | — | — | 20% | — | 5% | — |
| MC971 | 50% | — | — | — | 45% | — | 5% | — |
| MC972 | 87.5% | — | 7.5% | — | — | — | 5% | — |
| MC973 | 75% | — | 20% | — | — | — | 5% | — |
| MC974 | 50% | — | 45% | — | — | — | 5% | — |
| MC975 | 87.5% | — | — | 7.5% | — | — | 5% | — |
| MC976 | 75% | — | — | 20% | — | — | 5% | — |
| MC977 | 50% | — | — | 45% | — | — | 5% | — |
| MC978 | 87.5% | — | — | — | — | 7.5% | 5% | — |
| MC979 | 75% | — | — | — | — | 20% | 5% | — |
| MC980 | 50% | — | — | — | — | 45% | 5% | — |
| MC981 | 95% | — | — | — | — | — | 5% | — |
| MC982 | 100% | — | — | — | — | — | — | — |
| MC983 | 50% | 50% | — | — | — | — | — | — |
| MC984 | 50% | — | 50% | — | — | — | — | — |
| MC985 | 50% | — | — | 50% | — | — | — | — |

TABLE 4-continued

Alkyl enol ether cationic polymers mole percentage of polymer components

| polymer number | 2-Vinyloxyethyl Phthalimide | C2 | C3 | C4 | EG-C4 | Peg3-Me | C12 | C18 |
|---|---|---|---|---|---|---|---|---|
| MC986 | 50% | — | — | — | 50% | — | — | — |
| MC987 | 50% | — | — | — | — | 50% | — | — |

Preparation of biotinylated polymers (FIG. 16C): Polymer was brought up at 10 mg/ml in 0.1 M sodium bicarbonate and CY3-Osu at a 10/1 w/w ratio and allowed to react overnight to fluorescently label the polymer. The pH of solution was then readjusted to 8.0 with bicarb and a 1 to 10 weight percent of Biotion-PEG$_{3-100}$-CO2-NHS was added. The reaction ran 6–24 h and the polymers was purified on a G-25 column using 50 mM ammonium bicarbonate as eluting buffer. Purified polymers were then desalted by dialysis in 12,000–14,000 MWCO Cellulose tubing against distilled water (2×20 L, 48 h). The samples were then freeze dried.

2-propionic-3-methylmaleic anhydride modification of polymer: The biotinylated polymer was modified with 2-propionic-3-methylmaleic anhydride using 0.5–2 mol eq 2-propionic-3-methylmaleic anhydride per polymer primary amine in 10 mM HEPES, 500 mM diisopropylethylamine at pH 8.0 or higher. This polymer was purified using a G-25 spin column to remove unreacted 2-propionic-3-methylmaleic anhydride. This modification converted that polycation to a pH-labile polyanion.

Attachment of T7 ligand to the polymer: Streptavidin (20 mg, 10 mg/mL) was brought up in 75 mM Sodium Phosphate, 75 mM NaCl, 5mM EDTA, pH 7.2. To this solution was added 10–15 mole eq. of LC-SPDP (100 mg/mL in DMF, Pierce). The solution was gently shaken for 1 h at RT. The SPDP modified streptavidin was then purified using a G-25 column. It was determined that each streptavidin had 8–12 PDP groups attach (Pyridine-2-Thione Assay). To the PDP-modified streptavidin was added 3 mol eq of Cys-PEG$_{11}$-T7 ligand (MC920) Coupling of the T7 ligand to the streptavidin was allowed to continue for 24 hat 4° C. This conjugate was purified on G-25 column, freeze dried and brought up at 3.0 mg/mL in 25 mM MES, 125 mM NaCl, pH 6.0. These polymers may then be used to form complexes with polynucleotide to facilitate delivery of the polynucleotide to hepatocytes.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A composition for targeting hepatocytes comprising: a T7 ligand covalently attached to a compound, wherein,
   a) said T7 ligand is selected from the group consisting of: T7 p17 protein, modified T7 p17 protein, T7 p17 rod domain, T7 p17 coiled coil domain, SEQ ID NO: 1, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and
   b) said compound is selected from the group consisting of: drug, component of a drug or polynucleotide complex and polynucleotide.

2. The composition of claim 1 wherein the drug comprises interferon.

3. The composition of claim 1 wherein the complex consists of a liposome.

4. The composition of claim 1 wherein the complex consists of a polyplex.

5. The composition of claim 1 wherein the complex consists of a lipopolyplex.

6. The composition of claim 1 wherein the complex comprises a polynucleotide.

7. The composition of claim 6 wherein the polynucleotide consists of an expression cassette.

8. The composition of claim 6 wherein the polynucleotide consists of an RNA.

9. The composition of claim 1 wherein the polynucleotide consists of an RNA function inhibitor.

10. The composition of claim 1 wherein the T7 ligand contains a functional group.

11. The composition of claim 10 wherein the functional group consists of a thiol.

12. The composition of claim 11 wherein the thiol consists of a cysteine.

13. The composition of claim 10 wherein the functional group consists of biotin.

14. The composition of claim 10 wherein the functional group consists of streptavidin.

15. The composition of claim 1 wherein the T7 ligand is attached to the compound via a linker.

16. The composition of claim 15 wherein the linker consists of a polyethylene glycol.

17. The composition of claim 1 wherein the T7 ligand consists of: T7 ligand-cysteine-PDP-streptavidin.

18. The composition of claim 1 wherein the T7 ligand consists of T7 ligand-PEG-biotin.

19. A pharmaceutical preparation comprising: a compound selected from the group consisting of: drug, component of a drug or polynucleotide complex, and polynucleotide covalently attached to a T7 ligand selected from the group consisting of: T7 p17 protein, modified T7 p17 protein, T7 p17 rod domain, T7 p17 coiled coil domain, SEQ ID NO: 1, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24.

20. A composition for targeting hepatocytes in vivo comprising: a T7 ligand covalently attached to a compound, wherein
   a) said T7 ligand is selected from the group consisting of: T7 p17 protein, modified T7 p17 protein, T7 p17 rod domain, T7 p17 coiled coil domain, SEQ ID NO: 1, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and
   b) said compound is selected from the group consisting of: drug, component of a drug or polynucleotide complex and polynucleotide.

* * * * *

SEQUENCE LISTING

<160> NUMBER OF SEQ ID NOS: 36

<210> SEQ ID NO 1
<211> LENGTH: 33
<212> TYPE: PRT
<213> ORGANISM: Bacteriophage T7

<400> SEQUENCE: 1

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys Asn Thr Ala
            20                  25                  30

Gly

<210> SEQ ID NO 2
<211> LENGTH: 33
<212> TYPE: DNA
<213> ORGANISM: Bacteriophage T7

<400> SEQUENCE: 2
aaggaggtca tatggctaac gtaattaaaa ccg                               33

<210> SEQ ID NO 3
<211> LENGTH: 39
<212> TYPE: DNA
<213> ORGANISM: Bacteriophage T7

<400> SEQUENCE: 3
gattggatcc ttactcgttc tccaccatga ttgcattag         39

<210> SEQ ID NO 4
<211> LENGTH: 573
<212> TYPE: PRT
<213> ORGANISM: Bacteriophage T7

<400> SEQUENCE: 4

```
Met Gly Ser Ser His His His His His Ser Ser Gly Leu Val Pro
1               5                   10                  15

Arg Gly Ser His Met Ala Asn Val Ile Lys Thr Val Leu Thr Tyr Gln
            20                  25                  30

Leu Asp Gly Ser Asn Arg Asp Phe Asn Ile Pro Phe Glu Tyr Leu Ala
        35                  40                  45

Arg Lys Phe Val Val Thr Leu Ile Gly Val Asp Arg Lys Val Leu
    50                  55                  60

Thr Ile Asn Thr Asp Tyr Arg Phe Ala Thr Arg Thr Ile Ser Leu
65                  70                  75                  80

Thr Lys Ala Trp Gly Pro Ala Asp Gly Tyr Thr Thr Ile Glu Leu Arg
                85                  90                  95

Arg Val Thr Ser Thr Thr Asp Arg Leu Val Asp Phe Thr Asp Gly Ser
                100                 105                 110

Ile Leu Arg Ala Tyr Asp Leu Asn Val Ala Gln Ile Gln Thr Met His
            115                 120                 125

Val Ala Glu Glu Ala Arg Asp Leu Thr Thr Asp Thr Ile Gly Val Asn
    130                 135                 140

Asn Asp Gly His Leu Asp Ala Arg Gly Arg Ile Val Asn Leu Ala
145                 150                 155                 160

Asn Ala Val Asp Asp Arg Asp Ala Val Pro Phe Gly Gln Leu Lys Thr
                165                 170                 175

Met Asn Gln Asn Ser Trp Gln Ala Arg Asn Glu Ala Leu Gln Phe Arg
            180                 185                 190

Asn Glu Ala Glu Thr Phe Arg Asn Gln Ala Glu Gly Phe Lys Asn Glu
        195                 200                 205

Ser Ser Thr Asn Ala Thr Asn Thr Lys Gln Trp Arg Asp Glu Thr Lys
    210                 215                 220

Gly Phe Arg Asp Glu Ala Lys Arg Phe Lys Asn Thr Ala Gly Gln Tyr
225                 230                 235                 240

Ala Thr Ser Ala Gly Asn Ser Ala Ser Ala Ala His Gln Ser Glu Val
                245                 250                 255

Asn Ala Glu Asn Ser Ala Thr Ala Ser Ala Asn Ser Ala His Leu Ala
            260                 265                 270

Glu Gln Gln Ala Asp Arg Ala Glu Arg Glu Ala Asp Lys Leu Glu Asn
        275                 280                 285

Tyr Asn Gly Leu Ala Gly Ala Ile Asp Lys Val Asp Gly Thr Asn Val
    290                 295                 300

Tyr Trp Lys Gly Asn Ile His Ala Asn Gly Arg Leu Tyr Met Thr Thr
305                 310                 315                 320

Asn Gly Phe Asp Cys Gly Gln Tyr Gln Gln Phe Phe Gly Gly Val Thr
                325                 330                 335

Asn Arg Tyr Ser Val Met Glu Trp Gly Asp Glu Asn Gly Trp Leu Met
            340                 345                 350
```

```
Tyr Val Gln Arg Arg Glu Trp Thr Thr Ala Ile Gly Gly Asn Ile Gln
            355                 360                 365

Leu Val Val Asn Gly Gln Ile Ile Thr Gln Gly Gly Ala Met Thr Gly
    370                 375                 380

Gln Leu Lys Leu Gln Asn Gly His Val Leu Gln Leu Glu Ser Ala Ser
385                 390                 395                 400

Asp Lys Ala His Tyr Ile Leu Ser Lys Asp Gly Asn Arg Asn Asn Trp
                405                 410                 415

Tyr Ile Gly Arg Gly Ser Asp Asn Asn Asn Asp Cys Thr Phe His Ser
            420                 425                 430

Tyr Val His Gly Thr Thr Leu Thr Leu Lys Gln Asp Tyr Ala Val Val
            435                 440                 445

Asn Lys His Phe His Val Gly Gln Ala Val Ala Thr Asp Gly Asn
    450                 455                 460

Ile Gln Gly Thr Lys Trp Gly Gly Lys Trp Leu Asp Ala Tyr Leu Arg
465                 470                 475                 480

Asp Ser Phe Val Ala Lys Ser Lys Ala Trp Thr Gln Val Trp Ser Gly
                485                 490                 495

Ser Ala Gly Gly Gly Val Ser Val Thr Val Ser Gln Asp Leu Arg Phe
            500                 505                 510

Arg Asn Ile Trp Ile Lys Cys Ala Asn Asn Ser Trp Asn Phe Phe Arg
            515                 520                 525

Thr Gly Pro Asp Gly Ile Tyr Phe Ile Ala Ser Asp Gly Gly Trp Leu
            530                 535                 540

Arg Phe Gln Ile His Ser Asn Gly Leu Gly Phe Lys Asn Ile Ala Asp
545                 550                 555                 560

Ser Arg Ser Val Pro Asn Ala Ile Met Val Glu Asn Glu
                565                 570

<210> SEQ ID NO 5
<211> LENGTH: 160
<212> TYPE: PRT
<213> ORGANISM: Bacteriophage T7

<400> SEQUENCE: 5

Met Gly Ser Ser His His His His His His Ser Ser Gly Leu Val Pro
1               5                   10                  15

Arg Gly Ser His Pro Phe Gly Gln Leu Lys Thr Met Asn Gln Asn Ser
            20                  25                  30

Trp Gln Ala Arg Asn Glu Ala Leu Gln Phe Arg Asn Glu Ala Glu Thr
        35                  40                  45

Phe Arg Asn Gln Ala Glu Gly Phe Lys Asn Glu Ser Ser Thr Asn Ala
    50                  55                  60

Thr Asn Thr Lys Gln Trp Arg Asp Glu Thr Lys Gly Phe Arg Asp Glu
65                  70                  75                  80

Ala Lys Arg Phe Lys Asn Thr Ala Gly Gln Tyr Ala Thr Ser Ala Gly
                85                  90                  95

Asn Ser Ala Ser Ala Ala His Gln Ser Glu Val Asn Ala Glu Asn Ser
            100                 105                 110

Ala Thr Ala Ser Ala Asn Ser Ala His Leu Ala Glu Gln Gln Ala Asp
        115                 120                 125

Arg Ala Glu Arg Glu Ala Asp Lys Leu Glu Asn Tyr Asn Gly Leu Ala
    130                 135                 140

Gly Ala Ile Asp Lys Val Asp Gly Thr Asn Val Tyr Trp Lys Gly Asn
145                 150                 155                 160
```

<210> SEQ ID NO 6
<211> LENGTH: 309
<212> TYPE: PRT
<213> ORGANISM: Bacteriophage T7

<400> SEQUENCE: 6

Met Gly Ser Ser His His His His His Ser Ser Gly Leu Val Pro
1               5                   10                  15

Arg Gly Ser His Met Ala Asn Val Ile Lys Thr Val Leu Thr Tyr Gln
            20                  25                  30

Leu Asp Gly Ser Asn Arg Asp Phe Asn Ile Pro Phe Glu Tyr Leu Ala
        35                  40                  45

Arg Lys Phe Val Val Thr Leu Ile Gly Val Asp Arg Lys Val Leu
    50                  55                  60

Thr Ile Asn Thr Asp Tyr Arg Phe Ala Thr Arg Thr Ile Ser Leu
65                  70                  75                  80

Thr Lys Ala Trp Gly Pro Ala Asp Gly Tyr Thr Thr Ile Glu Leu Arg
                85                  90                  95

Arg Val Thr Ser Thr Thr Asp Arg Leu Val Asp Phe Thr Asp Gly Ser
                100                 105                 110

Ile Leu Arg Ala Tyr Asp Leu Asn Val Ala Gln Ile Gln Thr Met His
            115                 120                 125

Val Ala Glu Glu Ala Arg Asp Leu Thr Thr Asp Thr Ile Gly Val Asn
    130                 135                 140

Asn Asp Gly His Leu Asp Ala Arg Gly Arg Ile Val Asn Leu Ala
145                 150                 155                 160

Asn Ala Val Asp Asp Arg Asp Ala Val Pro Phe Gly Gln Leu Lys Thr
                165                 170                 175

Met Asn Gln Asn Ser Trp Gln Ala Arg Asn Glu Ala Leu Gln Phe Arg
            180                 185                 190

Asn Glu Ala Glu Thr Phe Arg Asn Gln Ala Glu Gly Phe Lys Asn Glu
        195                 200                 205

Ser Ser Thr Asn Ala Thr Asn Thr Lys Gln Trp Arg Asp Glu Thr Lys
    210                 215                 220

Gly Phe Arg Asp Glu Ala Lys Arg Phe Lys Asn Thr Ala Gly Gln Tyr
225                 230                 235                 240

Ala Thr Ser Ala Gly Asn Ser Ala Ser Ala Ala His Gln Ser Glu Val
                245                 250                 255

Asn Ala Glu Asn Ser Ala Thr Ala Ser Ala Asn Ser Ala His Leu Ala
            260                 265                 270

Glu Gln Gln Ala Asp Arg Ala Glu Arg Glu Ala Asp Lys Leu Glu Asn
        275                 280                 285

Tyr Asn Gly Leu Ala Gly Ala Ile Asp Lys Val Asp Gly Thr Asn Val
    290                 295                 300

Tyr Trp Lys Gly Asn
305

<210> SEQ ID NO 7
<211> LENGTH: 424
<212> TYPE: PRT
<213> ORGANISM: Bacteriophage T7

<400> SEQUENCE: 7

Met Gly Ser Ser His His His His His Ser Ser Gly Leu Val Pro
1               5                   10                  15

-continued

```
Arg Gly Ser His Pro Phe Gly Gln Leu Lys Thr Met Asn Gln Asn Ser
             20                  25                  30

Trp Gln Ala Arg Asn Glu Ala Leu Gln Phe Arg Asn Glu Ala Glu Thr
             35                  40                  45

Phe Arg Asn Gln Ala Glu Gly Phe Lys Asn Glu Ser Ser Thr Asn Ala
 50                  55                  60

Thr Asn Thr Lys Gln Trp Arg Asp Glu Thr Lys Gly Phe Arg Asp Glu
 65                  70                  75                  80

Ala Lys Arg Phe Lys Asn Thr Ala Gly Gln Tyr Ala Thr Ser Ala Gly
             85                  90                  95

Asn Ser Ala Ser Ala Ala His Gln Ser Glu Val Asn Ala Glu Asn Ser
            100                 105                 110

Ala Thr Ala Ser Ala Asn Ser Ala His Leu Ala Glu Gln Gln Ala Asp
            115                 120                 125

Arg Ala Glu Arg Glu Ala Asp Lys Leu Glu Asn Tyr Asn Gly Leu Ala
130                 135                 140

Gly Ala Ile Asp Lys Val Asp Gly Thr Asn Val Tyr Trp Lys Gly Asn
145                 150                 155                 160

Ile His Ala Asn Gly Arg Leu Tyr Met Thr Thr Asn Gly Phe Asp Cys
            165                 170                 175

Gly Gln Tyr Gln Gln Phe Phe Gly Gly Val Thr Asn Arg Tyr Ser Val
            180                 185                 190

Met Glu Trp Gly Asp Glu Asn Gly Trp Leu Met Tyr Val Gln Arg Arg
            195                 200                 205

Glu Trp Thr Thr Ala Ile Gly Gly Asn Ile Gln Leu Val Val Asn Gly
            210                 215                 220

Gln Ile Ile Thr Gln Gly Gly Ala Met Thr Gly Gln Leu Lys Leu Gln
225                 230                 235                 240

Asn Gly His Val Leu Gln Leu Glu Ser Ala Ser Asp Lys Ala His Tyr
            245                 250                 255

Ile Leu Ser Lys Asp Gly Asn Arg Asn Asn Trp Tyr Ile Gly Arg Gly
            260                 265                 270

Ser Asp Asn Asn Asn Asp Cys Thr Phe His Ser Tyr Val His Gly Thr
            275                 280                 285

Thr Leu Thr Leu Lys Gln Asp Tyr Ala Val Val Asn Lys His Phe His
            290                 295                 300

Val Gly Gln Ala Val Val Ala Thr Asp Gly Asn Ile Gln Gly Thr Lys
305                 310                 315                 320

Trp Gly Gly Lys Trp Leu Asp Ala Tyr Leu Arg Asp Ser Phe Val Ala
            325                 330                 335

Lys Ser Lys Ala Trp Thr Gln Val Trp Ser Gly Ser Ala Gly Gly Gly
            340                 345                 350

Val Ser Val Thr Val Ser Gln Asp Leu Arg Phe Arg Asn Ile Trp Ile
            355                 360                 365

Lys Cys Ala Asn Asn Ser Trp Asn Phe Phe Arg Thr Gly Pro Asp Gly
370                 375                 380

Ile Tyr Phe Ile Ala Ser Asp Gly Gly Trp Leu Arg Phe Gln Ile His
385                 390                 395                 400

Ser Asn Gly Leu Gly Phe Lys Asn Ile Ala Asp Ser Arg Ser Val Pro
            405                 410                 415

Asn Ala Ile Met Val Glu Asn Glu
            420
```

```
<210> SEQ ID NO 8
<211> LENGTH: 31
<212> TYPE: DNA
<213> ORGANISM: Aequorea victoria

<400> SEQUENCE: 8
cggtcgccca tggtgagc aagggcgagg a                              31

<210> SEQ ID NO 9
<211> LENGTH: 36
<212> TYPE: DNA
<213> ORGANISM: Aequorea victoria

<400> SEQUENCE: 9
gattatgatc atatgtctag atccggtgga tcctac                       36

<210> SEQ ID NO 10
<211> LENGTH: 43
<212> TYPE: DNA
<213> ORGANISM: Homo sapiens

<400> SEQUENCE: 10
gctgctctca tatgtgtgat ctgcctcaaa cccacagcct ggg               43

<210> SEQ ID NO 11
<211> LENGTH: 52
<212> TYPE: DNA
<213> ORGANISM: Homo sapiens

<400> SEQUENCE: 11
tgaaccagca tatgttcctt acttcttaaa ctttcttgca gtttgttga ca      52

<210> SEQ ID NO 12
<211> LENGTH: 36
<212> TYPE: DNA
<213> ORGANISM: Bacteriophage T7

<400> SEQUENCE: 12
ggaattccat atgtgtgatg ctgttccgtt tggtca                       36

<210> SEQ ID NO 13
<211> LENGTH: 32
<212> TYPE: DNA
<213> ORGANISM: Bacteriophage T7

<400> SEQUENCE: 13
cgcggatcct tagtattgac cagccgtatt ct                           32

<210> SEQ ID NO 14
<211> LENGTH: 33
<212> TYPE: PRT
<213> ORGANISM: Bacteriophage T7

<400> SEQUENCE: 14

Lys Asn Glu Ser Ser Thr Asn Ala Thr Asn Thr Lys Gln Trp Arg Asp
1               5                   10                  15

Glu Thr Lys Gly Phe Arg Asp Glu Ala Arg Arg Phe Lys Asn Thr Ala
            20                  25                  30

Gly
```

```
<210> SEQ ID NO 15
<211> LENGTH: 33
<212> TYPE: PRT
<213> ORGANISM: Bacteriophage T7

<400> SEQUENCE: 15

Lys Asn Glu Ser Ser Thr Asn Ala Thr Asn Thr Lys Gln Trp Lys Asp
1               5                   10                  15

Glu Thr Lys Gly Phe Arg Asp Glu Ala Lys Arg Phe Lys Asn Thr Ala
            20                  25                  30

Gly

<210> SEQ ID NO 16
<211> LENGTH: 40
<212> TYPE: PRT
<213> ORGANISM: Bacteriophage T7

<400> SEQUENCE: 16

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys Asn Thr Ala
            20                  25                  30

Gly Gln Tyr Ala Thr Ser Ala Gly
        35                  40

<210> SEQ ID NO 17
<211> LENGTH: 33
<212> TYPE: PRT
<213> ORGANISM: Bacteriophage T7

<400> SEQUENCE: 17

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys Asp Glu Ala
            20                  25                  30

Gly

<210> SEQ ID NO 18
<211> LENGTH: 28
<212> TYPE: PRT
<213> ORGANISM: Bacteriophage T7

<400> SEQUENCE: 18

Thr Asn Ala Thr Asn Thr Lys Gln Trp Arg Asp Glu Thr Lys Gly Phe
1               5                   10                  15

Arg Asp Glu Ala Lys Arg Phe Lys Asn Thr Ala Gly
            20                  25

<210> SEQ ID NO 19
<211> LENGTH: 29
<212> TYPE: PRT
<213> ORGANISM: Bacteriophage T7

<400> SEQUENCE: 19

Ser Thr Asn Ala Thr Asn Thr Lys Gln Trp Arg Asp Glu Thr Lys Gly
1               5                   10                  15

Phe Arg Asp Glu Ala Lys Arg Phe Lys Asn Thr Ala Gly
            20                  25
```

```
<210> SEQ ID NO 20
<211> LENGTH: 30
<212> TYPE: PRT
<213> ORGANISM: Bacteriophage T7

<400> SEQUENCE: 20

Ser Ser Thr Asn Ala Thr Asn Thr Lys Gln Trp Arg Asp Glu Thr Lys
1               5                   10                  15
Gly Phe Arg Asp Glu Ala Lys Arg Phe Lys Asn Thr Ala Gly
            20                  25                  30

<210> SEQ ID NO 21
<211> LENGTH: 31
<212> TYPE: PRT
<213> ORGANISM: Bacteriophage T7

<400> SEQUENCE: 21

Glu Ser Ser Thr Asn Ala Thr Asn Thr Lys Gln Trp Arg Asp Glu Thr
1               5                   10                  15
Lys Gly Phe Arg Asp Glu Ala Lys Arg Phe Lys Asn Thr Ala Gly
            20                  25                  30

<210> SEQ ID NO 22
<211> LENGTH: 33
<212> TYPE: PRT
<213> ORGANISM: Bacteriophage T7

<400> SEQUENCE: 22

Lys Asn Glu Ser Ser Thr Asn Ala Thr Asn Thr Lys Gln Trp Arg Asp
1               5                   10                  15
Glu Thr Lys Gly Phe Arg Asp Glu Ala Lys Arg Phe Lys Asn Thr Ala
            20                  25                  30
Gly

<210> SEQ ID NO 23
<211> LENGTH: 33
<212> TYPE: PRT
<213> ORGANISM: Bacteriophage T7

<400> SEQUENCE: 23

Lys Asn Glu Ser Ser Thr Asn Ala Thr Asn Thr Lys Gln Trp Arg Asp
1               5                   10                  15
Glu Thr Lys Gly Phe Arg Asp Glu Ala Lys Arg Phe Lys Asn Thr Ala
            20                  25                  30
Gly

<210> SEQ ID NO 24
<211> LENGTH: 28
<212> TYPE: PRT
<213> ORGANISM: Bacteriophage T7

<400> SEQUENCE: 24

Lys Asn Glu Ser Ser Thr Asn Ala Thr Asn Thr Lys Gln Trp Arg Asp
1               5                   10                  15
Glu Thr Lys Gly Phe Arg Asp Glu Ala Lys Arg Phe
            20                  25

<210> SEQ ID NO 25
<211> LENGTH: 33
<212> TYPE: PRT
<213> ORGANISM: Bacteriophage T7
```

-continued

```
<400> SEQUENCE: 25

Lys Asn Glu Ser Ser Thr Asn Ala Thr Asn Thr Lys Gln Trp Arg Asp
1               5                   10                  15

Glu Thr Lys Gly Phe Arg Asp Glu Ala Glu Arg Phe Lys Asn Thr Ala
            20                  25                  30

Gly

<210> SEQ ID NO 26
<211> LENGTH: 33
<212> TYPE: PRT
<213> ORGANISM: Bacteriophage T7

<400> SEQUENCE: 26

Arg Asn Glu Ser Ser Thr Asn Ala Thr Asn Thr Lys Gln Trp Arg Asp
1               5                   10                  15

Glu Thr Lys Gly Phe Arg Asp Glu Ala Arg Arg Phe Arg Asn Thr Ala
            20                  25                  30

Gly

<210> SEQ ID NO 27
<211> LENGTH: 33
<212> TYPE: PRT
<213> ORGANISM: Bacteriophage T7

<400> SEQUENCE: 27

Lys Asn Glu Ser Ser Thr Asn Ala Thr Asn Thr Arg Gln Trp Arg Asp
1               5                   10                  15

Glu Thr Arg Gly Phe Arg Asp Glu Ala Arg Arg Phe Lys Asn Thr Ala
            20                  25                  30

Gly

<210> SEQ ID NO 28
<211> LENGTH: 25
<212> TYPE: PRT
<213> ORGANISM: Bacteriophage T7

<400> SEQUENCE: 28

Lys Asn Glu Ser Ser Thr Asn Ala Thr Asn Thr Lys Gln Trp Arg Asp
1               5                   10                  15

Glu Thr Lys Gly Phe Arg Asp Glu Ala
            20                  25

<210> SEQ ID NO 29
<211> LENGTH: 25
<212> TYPE: PRT
<213> ORGANISM: Bacteriophage T7

<400> SEQUENCE: 29

Ser Ser Thr Asn Ala Thr Asn Thr Lys Gln Trp Arg Asp Glu Thr Lys
1               5                   10                  15

Gly Phe Arg Asp Glu Ala Lys Arg Phe
            20                  25

<210> SEQ ID NO 30
<211> LENGTH: 28
<212> TYPE: PRT
<213> ORGANISM: Bacteriophage T7
```

-continued

```
<400> SEQUENCE: 30

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe
            20                  25

<210> SEQ ID NO 31
<211> LENGTH: 15
<212> TYPE: PRT
<213> ORGANISM: Bacteriophage T7

<400> SEQUENCE: 31

Lys Gly Phe Arg Asp Glu Ala Lys Arg Phe Lys Asn Thr Ala Gly
1               5                   10                  15

<210> SEQ ID NO 32
<211> LENGTH: 22
<212> TYPE: PRT
<213> ORGANISM: Bacteriophage T7

<400> SEQUENCE: 32

Lys Gln Trp Arg Asp Glu Thr Lys Gly Phe Arg Asp Glu Ala Lys Arg
1               5                   10                  15

Phe Lys Asn Thr Ala Gly
            20

<210> SEQ ID NO 33
<211> LENGTH: 29
<212> TYPE: PRT
<213> ORGANISM: Bacteriophage T7

<400> SEQUENCE: 33

Leu Lys Thr Met Asn Gln Asn Ser Trp Gln Ala Arg Asn Glu Ala Leu
1               5                   10                  15

Gln Phe Arg Asn Glu Ala Glu Thr Gly Arg Asn Gln Ala
            20                  25

<210> SEQ ID NO 34
<211> LENGTH: 33
<212> TYPE: PRT
<213> ORGANISM: Bacteriophage T7

<400> SEQUENCE: 34

Ala Thr Asn Thr Lys Gln Trp Arg Asp Glu Thr Lys Gly Phe Arg Asp
1               5                   10                  15

Glu Ala Lys Arg Phe Lys Asn Thr Ala Gly Gln Tyr Ala Thr Ser Ala
            20                  25                  30

Gly

<210> SEQ ID NO 35
<211> LENGTH: 27
<212> TYPE: PRT
<213> ORGANISM: Bacteriophage T7

<400> SEQUENCE: 35

Asn Ala Thr Asn Thr Lys Gln Trp Arg Asp Glu Thr Lys Gly Phe Arg
1               5                   10                  15

Asp Glu Ala Lys Arg Phe Lys Asn Thr Ala Gly
            20                  25
```

```
<210> SEQ ID NO 36
<211> LENGTH: 33
<212> TYPE: PRT
<213> ORGANISM: Bacteriophage T7

<400> SEQUENCE: 36

Lys Asn Glu Ser Ser Thr Asn Ala Thr Asn Thr Lys Gln Trp Arg Asp
1               5                   10                  15

Glu Thr Lys Gly Phe Arg Asp Glu Ala Lys Arg Phe Lys Asn Thr Ala
            20                  25                  30

Gly
```